(12) United States Patent
Nemunaitis et al.

(10) Patent No.: US 9,695,422 B2
(45) Date of Patent: *Jul. 4, 2017

(54) FURIN-KNOCKDOWN BI-FUNCTIONAL RNA

(71) Applicant: GRADALIS, INC., Dallas, TX (US)

(72) Inventors: John J. Nemunaitis, Cedar Hill, TX (US); Neil Senzer, Delray Beach, FL (US); Phillip B. Maples, Pilot Point, TX (US); Donald Rao, Dallas, TX (US)

(73) Assignee: GRADALIS, INC., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/844,912

(22) Filed: Sep. 3, 2015

(65) Prior Publication Data

US 2015/0368651 A1    Dec. 24, 2015

Related U.S. Application Data

(63) Continuation of application No. 12/973,787, filed on Dec. 20, 2010, now Pat. No. 9,157,084.

(60) Provisional application No. 61/289,661, filed on Dec. 23, 2009.

(51) Int. Cl.
| | | |
|---|---|---|
| *C12N 15/00* | (2006.01) | |
| *C07H 21/04* | (2006.01) | |
| *C07K 1/00* | (2006.01) | |
| *C12N 15/113* | (2010.01) | |
| *A61K 38/21* | (2006.01) | |
| *C12N 15/85* | (2006.01) | |
| *C07K 14/535* | (2006.01) | |
| *A61K 38/19* | (2006.01) | |
| *A61K 48/00* | (2006.01) | |

(52) U.S. Cl.
CPC ........ *C12N 15/1137* (2013.01); *A61K 38/193* (2013.01); *A61K 38/217* (2013.01); *A61K 48/005* (2013.01); *C07K 14/535* (2013.01); *C12N 15/85* (2013.01); *C12N 2310/14* (2013.01); *C12N 2310/141* (2013.01); *C12N 2310/3519* (2013.01); *C12N 2310/531* (2013.01); *C12N 2320/31* (2013.01); *C12N 2320/35* (2013.01); *C12N 2330/51* (2013.01); *C12N 2830/20* (2013.01); *C12N 2840/107* (2013.01)

(58) Field of Classification Search
None
See application file for complete search history.

(56) References Cited

U.S. PATENT DOCUMENTS

| | | |
|---|---|---|
| 6,506,559 B1 | 1/2003 | Driver et al. |
| 7,763,461 B2 | 7/2010 | Link, Jr. et al. |
| 7,763,722 B2 | 7/2010 | Chang et al. |
| 7,893,034 B2 | 2/2011 | Slack et al. |
| 8,119,395 B1 | 2/2012 | Weiner et al. |
| 8,252,526 B2 | 8/2012 | Rao |
| 8,361,983 B2 | 1/2013 | Nemunaitis et al. |
| 8,735,058 B2 | 5/2014 | Rao |
| 8,758,998 B2 | 6/2014 | Rao |
| 9,132,146 B2 | 9/2015 | Nemunaitis et al. |
| 9,157,084 B2 | 10/2015 | Nemunaitis et al. |
| 2003/0138407 A1 | 7/2003 | Lu et al. |
| 2003/0144823 A1 | 7/2003 | Fox et al. |
| 2004/0023390 A1 | 2/2004 | Davidson et al. |
| 2004/0088116 A1 | 5/2004 | Khalil et al. |
| 2004/0213764 A1 | 10/2004 | Wold et al. |
| 2004/0241854 A1 | 12/2004 | Davidson et al. |
| 2004/0242518 A1 | 12/2004 | Chen et al. |
| 2004/0243354 A1 | 12/2004 | Periwal |
| 2005/0043263 A1 | 2/2005 | Giese et al. |
| 2005/0080031 A1 | 4/2005 | McSwiggen |
| 2005/0142578 A1 | 6/2005 | Usman et al. |
| 2005/0143333 A1 | 6/2005 | Richards et al. |
| 2005/0245508 A1 | 11/2005 | Weller et al. |
| 2005/0272664 A1 | 12/2005 | McColl et al. |
| 2007/0179113 A1 | 8/2007 | Bauzon et al. |
| 2007/0224194 A1 | 9/2007 | McColl et al. |
| 2008/0269474 A1 | 10/2008 | Rao |
| 2010/0087625 A1 | 4/2010 | Peel et al. |
| 2011/0045534 A1 | 2/2011 | Cheung et al. |
| 2011/0150832 A1 | 6/2011 | Nemunaitis et al. |
| 2013/0071928 A1 | 3/2013 | Rao |

(Continued)

FOREIGN PATENT DOCUMENTS

| | | |
|---|---|---|
| CA | 1341197 C | 3/2001 |
| WO | WO-03006477 A1 | 1/2003 |

(Continued)

OTHER PUBLICATIONS

Ardeshna, Kirit M., et al., "The PI3 Kinase, p38 SAP Kinase, and NF-kB Signal Transduction Pathway Involved in the Survival and Maturation of Lipopolysaccharide-Stimulated Human Monocyte—Derived Dendritic Cells," Blood, Aug. 1, 2000, vol. 96, No. 3, pp. 1039-1046.

Ashcroft, Gillian S., "Bidirectional Regulation of Macrophage Function by TGF-B," Microbes and Infection, 1999, pp. 1275-1282.

Azuma-Mukal, Asuka, et al., "Characterization of Endogenous Human Argonautes and their miRNA Partners in RNA Silencing," PNAS, Jun. 10, 2008, vol. 105, No. 23, pp. 7964-7969.

Banchereau, Jacques, et al., "Immunobiology of Dendritic Cells," Annu. Rev. Immunol., (2000), 18:767-811.

(Continued)

*Primary Examiner* — Richard Schnizer
(74) *Attorney, Agent, or Firm* — Wilson Sonsini Goodrich & Rosati

(57) ABSTRACT

Compositions and methods to attenuate the immunosuppressive activity of TGF-β through the use of bi-functional shRNAs is described herein. The bi-functional shRNAs of the present invention knocks down the expression of furin in cancer cells to augment tumor antigen expression, presentation, and processing through expression of the GM-CSF transgene.

18 Claims, 7 Drawing Sheets

(56) References Cited

U.S. PATENT DOCUMENTS

| | | | |
|---|---|---|---|
| 2013/0078279 | A1 | 3/2013 | Nemunaitis et al. |
| 2015/0329873 | A1 | 11/2015 | Nemunaitis et al. |

FOREIGN PATENT DOCUMENTS

| | | |
|---|---|---|
| WO | WO-2006086838 A1 | 8/2006 |
| WO | WO-2011079070 A1 | 6/2011 |

OTHER PUBLICATIONS

Bassi, Daniel E., et al., "Elevated Furin Expression in Aggressive Human Head and Neck Tumors and Tumor Cell Lines," Molecular Carcinogenesis, (2001), 31:224-232.

Bassi, Daniel E., et al., "The Proprotein Convertases Furin and PACE4 Play a Significant Role in Tumor Progression," Molecular Carcinogenesis, (2000), 28:63-69.

Yuan, Bingbing, et al., "siRNA Selection Server: an automated siRNA oligonucleotide prediction server," Nucleic Acids Research, 2004, vol. 32.

Bommireddy, Ramireddy, et al., "TGFB1 and Treg Cells: Alliance for Tolerance," Trends Mol. Med., Nov. 13, 2007, 13(11):492-501.

Border, Wayne A., et al., "Transforming Growth Factor-B in Disease: The Dark Side of Tissue Repair," J. Clin. Invest., Jul. 1992, vol. 90, 7 pages.

Cheng, Min, et al., "Pro-Protein Convertase Gene Expression in Human Breast Cancer," Int. J. Cancer, (1997), 71:966-971.

Dranoff, Glenn, et al., "Vaccination with Irradiated Tumor Cells Engineered to Secrete Murine Granulocyte-Machrophage Colony—Stimulating Factor Stimulates Potent, Specific, and Long-Lasting Anti-Tumor Immunity," Proc. Natl. Acad. Sci., Apr. 1993, vol. 90, pp. 3539-3543.

Du Caigan, et al., "Mechanism of Inhibition of LPS-Induced IL-12p40 Production by IL-10 and TGF-Bin ANA-1 Cells," Journal of Leukocyte Biology, Jul. 1998, vol. 64, pp. 92-97.

Jackowlew, Sonia, et al., "Expression of Transforming Growth Factor B Ligand and Receptor Messenger RNAs in Lung Cancer Cell Lines," Cell Growth & Differentiation, Apr. 1995, vol. 6, pp. 465-476.

Kumar, Padma, et al., "TAG Xenograft Vaccine: Xenograft-Expanded Autologous Tumor Vaccine Genetically Modified to Express GM-CSF and Block Production of TGFB2," Bio Processing Journal, (2009).

Fantini, Massimo, et al., "Cutting Edge: TGF-B Induces a Regulatory Phenotype in CD4+CD25-T Cells Through Foxp3 Induction and Down Regulation of Smad7," J. Immunol., (2004), 172:5149-5153.

Fogel-Petrovic, Mirjana, et al., "Physiological Concentrations of Transforming Growth Factor B1 Selectively Inhibit Human Dendritic Cell Function," International Immunopharmacology, (2007), 7:1924-1933.

Funston, Garth M., et al., "Expression of Heterologous Genes in Oncolytic Adenoviruses Using Picornavital 2A Sequences that Trigger Ribosome Skipping," Journal of General Virology, (2008), 89:389-396.

Geissmann, Frederic, et al., "TGF-B1 Prevents the Noncognate maturation of Human Dendritic Langerhans Cells," J. Immunol., (1999), 162:4567-4575.

Hege, Kristen M., et al., "GM-CSF Gene-Modified Cancer Cell Immunotherapies: Of Mice and Men," International Reviews of Immunology, (2006), 25:321-352.

Henrich, Stefan, et al., "The Crystal Structure of the Proprotein Processing Proteinase Furin Explains its Stringent Specificity," Jul. 2003, vol. 10, No. 7, pp. 520-527.

Hodi, F. Stephen, et al., "Immunologic and Clinical Effects of Antibody Blockade of Cytotoxic T Lymphocyte-Associated Antigen Previously Vaccinated Cancer Patients," PNAS, Feb. 26, 2008, vol. 105, No. 8, pp. 3005-3010.

International Search and Written Opinion for PCT/2010/061309, dated Feb. 23, 2011, 5 pages.

Hu, Xiaotang, et al., "Characterization of a Unique Factor—Independent Variant Derived from Human Factor-Dependent TF-1 Cells: A Transformed Event," Leukemia Research, (1998), 22:817-826.

Jackson, Scott A., et al., "Self-Splicing of a Group I Intron Reveals Partitioning of Native and Misfolded RNA Populations in Yeast," RNA, (2006), 12:2149-2159.

Khatib, Abdel-Majid, et al., "Proprotein Convertases in Tumor Progression and Malignancy," American Journal of Pathology, Jun. 2002, vol. 160, No. 6, pp. 1921-1934.

Leuschner, Philipp J.F., et al., "Cleavage of the siRNA Passenger Strand During RISC Assembly in Human Cells," EMBO Reports, (2006), vol. 7, No. 3, pp. 314-320.

Levy, Laurence, et al., "Alterations in Components of the TGF-B Superfamily Signaling Pathways in Human Cancer," Cytokine & Growth Factor Reviews, (2006), 17:41-58.

Li, Ming O., et al., "Transforming Growth Factor-B Regulation of Immune Responses," Annu. Rev. Immunol., (2006), 24:99-146.

Lopez de Cicco, Ricardo, et al., "Human Carcinoma Cell Growth and Invasiveness is Impaired by the Propeptide of the Ubiquitous Proprotein Convertase Furin," Cancer Research, May 15, 2005, 65:(10):4162-4171.

Lu, Jun, et al., "TAP—Independent Presentation of CTL Epitopes by Trojan Antigens," J. Immunol., (2001), 166:7063-7071.

Matranga, Christian, et al., "Passenger-Strand Cleavage Facilitates Assembly of siRNA into Ago2-Containing RNAi Enzyme Complexes," Cell, Nov. 18, 2005, vol. 123, pp. 607-620.

Mbikay, M., et al., "Comparative Analysis of Expression of the Proprotein Convertases Furin, PACE4, PC1 and PC2 in Human Lung Tumours," British Journal of Cancer, (1997), 75(10), pp. 1509-1514.

Montenegro, D.E., et al., "TGFB Inhibits GM-CSF-Induced Phosphorylation of ERK and MEK in Human Myeloid Leukemia Cell Lines via Inhibition of Phosphatidylinositol 3-Kinase (P13-k)," Cell Proliferation, (2009), 42:1-9.

Naganuma, Hirofumi, et al., "Transforming Growth Factor-B Inhibits Interferon-y Secretion by Lymphokine-Activated Killer Cells Stimulated with Tumor Cells," Neurol. Med. Chir., (1996), 36:789-795.

Nemunaitis, J., et al., "Phase 1/2 Trial of Autologous Tumor Mixed with an Allogeneic GVAX Vaccine in Advanced-Stage Non-Small-cell Lung Cancer," Cancer Gene Therapy, (2006), 13:555-562.

Nemunaitis, John, "GVAX (GMCSF Gene Modified Tumor Vaccine) in Advanced Stage Non Small Cell Lung Cancer," Journal of Controlled Release, (2003), 91:225-231.

Nemunaitis, J., et al., "A Review of Vaccine Clinical Trials for Non-Small Cell Lung Cancer," Expert Opin. Biol. Ther., (2007), 7(1):89-102.

Nemunaitis, John, et al., "Phase II Study of Belagenpumatucel-L, a Transforming Growth Factor Beta-2 Antisense Gene-Modified Allogeneic Tumor Cell Vaccine in Non-Small-Cell Lung Cancer," Journal of Clinical Oncology, Oct. 10, 2008, vol. 24, No. 29, pp. 4721-4730.

Page, Robert E., et al., "Increased Expression of the Pro-Protein Convertase Furin Predicts Decreased Survival in Ovarian Cancer," Cellular Oncology, (2007), 29:289-299.

Pearton, David J., et al., "Proprotein Convertase Expression and Localization in Epidermis: Evidence for Multiple Roles and Substrates," Exp. Dermatol, (2001), 10:193-203.

Pesu, Marko, et al., "T Cell-Expressed Proprotein Convertase Furin is Essential for Maintenance of Peripheral Tolerance," Nature, Sep. 11, 2008, 455(7210), pp. 246-250.

Pesu, Marko, et al., "Proprotein Convertase Furin is Preferentially Expressed in T Helper 1 Cells and Regulates Interferon Gamma," Blood, Apr. 20, 2006, 108:983-985.

Polak, Me, et al., "Mechanisms of Local Immunosuppression in Cutaneous Melanoma," British Journal of Cancer, (2007), 96:1879-1887.

Rana, Shushan, et al., "Stathmin 1: A Novel Therapeutic Target for Anticancer Activity," Expert Reviews, (2008), pp. 1461-1470.

Rao, D.et al., "siRNA vs shRNA: Similarities and Differences", Advanced Drug Delvery Reviews, 61, 2009, 746-859.

(56) References Cited

OTHER PUBLICATIONS

Rao, DD, et al., "Enhanced Target Gene Knockdown by a Bifunctional shRNA: A Novel Approach of RNA Interference," Cancer Gene Therapy, (2010), 12 pages.
Takeuchi, Masaru, et al., "TGF-B Promotes Immune Deviation by Altering Accessory Signals of Antigen-Presenting Cells," J Immunol, (1998) 160;1589-1597.
Romero, Pedro, "Current State of Vaccine Therapies in Non-Small-Cell Lung Cancer," Clinical Lung Cancer, (2008), vol. 9, Suppl. 1, pp. S28-S36.
Schalken, Jack A., et al., "fur Gene Expression as a Discriminating Marker for Small Cell and Nonsmall Cell Lung Carcinomas," J. Clin. Invest., Dec. 1987, vol. 80, pp. 1545-1549.
Thomas, Dori A., et al., "TGF-B Directly Targets Cytotoxic T Cell Functions During Tumor Evasion of Immune Surveillance," Cancer Cell, Nov. 2005, vol. 8, pp. 369-380.
Thomas, Gary, "Furin at the Cutting Edge: From Protein Traffic to Embryogenesis and Disease," Nat. Rev. Mol. Cell Biol., (Oct. 2002), 3(10):753-766.
Tong, Alex W., et al., "Intratumoral Injection of INGN 241, a Nonreplicating Adenovector Expressing the Melanoma-Differentiation Associated Gene-7 (mda-7/IL24): Biologic Outcome in Advanced Cancer Patients," Molecular Therapy, Jan. 2005, vol. 11, No. 1, pp. 160-172.
Tsunawaki, Shohko, et al., "Deactivation of Macrophages by Transforming Growth Factor-B," Jul. 21, 1988, vol. 334, pp. 260-262.
Wick, Wolfgang, et al., "Transforming Growth Factor-B: A Molecular Target for the Future Therapy of Glioblastoma," Current Pharmaceutical Design, (2006), 12:341-349.
Yamaguchi, Yasunori, et al., "Contrasting Effects of TGF-B1 and TNF-a on the Development of Dendritic Cells from Progenitors in Mouse Bone Marrow," Stem Cells, (1997), 15:144-153.
Bassi et al. "Furin Inhibition Results in Absent or Decreased Invasiveness and Tumorigenicity of Human Cancer Cells", Department of Pathology, Aug. 28, 2001, vol. 18.
Leitlein, S. et al. "Processing of Immunosuppressive Pro-TGF-B 1,2 by Human Glioblastoma Cells Involves Cytoplasmic and Secreted Furin-Like Proteases", J Immunol 2001, vol. 166, pp. 7238-7243.
Mercapide, J. et al., "Inhibition of Furin—Mediated processing Results in Suppression of Astrocytoma Cell Growth and Invasiveness", Clin Cancer Res 2002, vol. 8, pp. 1740-1746.
Slooten, M.L. et al., "Liposomes Containing Interferon—Gamma as Adjuvant in Tumor Cell Vaccines", Pahrmaceutical Research, vol. 17, No. 1, 2000.
Borrello et al., "GM-CSF-Based Cellular Vaccines: A Review of the Clinical Experience", John Hopkins Oncology, vol. 213, 2001, pp. 185-193.
Burghardt et al., "Pirfenidone Inhibits TGF-B Expression in Malignant Glioma Cells", Biochemical and Biophysical Research, 354, 2007, pp. 542-547.
Arteaga, "Inhibition of TGFB Signalling in Cancer Therapy", Current Opinion in Genetics, vol. 16, 2006, pp. 30-37.
Friedman et al., High Levels of Transforming Growth Factor Beta 1 Correlate with Disease Progression in Human Colon Cancer Cancer Epidemiol Biomarkers, vol. 4, 1995, pp. 549-554.
Lagos-Quintana et al., "Identification of Novel Genes Coding for Small Expressed RNAs", Science, vol. 294, 2001.
Kong, et al., "Elevated Plasma Transforming Growth Factor-B1 Levels in Breast Cancer Patients Decrease After Surgical Removal of the Tumor"., Annals of Surgery, vol. 222, No. 2, pp. 155-162, 1995.
Mcmahon, et al., "Altrenative Pathway for the Role of Furin in Tumor Cell Invasion Process Enhanced MMP-2 Levels Through Bioactive TGFB", Experimental Cell Research, vol. 291, pp. 326-339, 2003.
Olivares et al., "Phase I Trial of TGF-B2 Antisense GM-CSF Gene-Modified Autologous Tumor Cell (TAG Vaccine", Clin Cancer Res, vol. 17, pp. 183-192, 2011.

Penafuerte et al., "Novel TGF-B Antagonist Inhibits Tumor Growth and Angiogenesis by Inducing IL-2 Receptor-Driven STAT1 Activation", May 6, 2011, doi:10.4049/jimmuno1.1003816.
Scamuffa et al.,"Selective Inhibition of Proprotein Convertases Represses the metastatic Potential of Human Colorectal Tumor Cells", Journal of Clinicallnvestigation, vol. 118, No. 1, 2008.
Maples, Phillip, et al., "TAG Vaccine: Autologous Tumor Vaccine Genetically Modified to Express GM-CSF and Block Production of TGFB2," Bio Processing Journal, (2009).
Maples, Phillip, et al., "FANG Vaccine: Autologous Tumor Cell Vaccine Genetically Modified to Express GM-CSF and Block Production of Furin," Bio Processing Journal, (2009).
Zeng, Yan, et al., "Structural requirements for pre-microRNA binding and nuclear export by Exportin 5," Nucleic Acids Research, 2004, vol. 32.
WilBio Conference 2007, Cellular Products for Vaccines, herapies and Tissue Regeneration.
Aleman et al. Comparison of siRNA-induced off-target RNA and Protein Effects. Cold Spring Harbor Laboratory Press 13:385-395 (2007).
Ameres et al. Molecular Basis for Target RNA Recognition and Cleavage by HumanRISC. Cell 130:101-112 (2007).
Bierie et al. Tumour microenvironment: TGFβ: The Molecular Jekyll and Hyde of Cancer. Nature Reviews 6:506-520 (Jul. 2006) (Abstract).
Burnett et al. Current progress of siRNA/shRNA therapeutics in clinical trials. Biotech J 6:1130-1146 (2011).
Carette et al. Conditionally Replicating Adenoviruses Expressing Short Hairpin RNAs Silence the Expression of a Target Gene in Cancer Cells. Cancer Res 64:2663-2667 (Apr. 15, 2004).
Chapman et al. Effect of intron a from human cytomegalovirus (Towne) immediate-early gene on heterologous expression in mammalian cells. Nucleic Acids Res 19:3979-3986 (1991).
Davidson et al. Current Prospects for RNA Interference-Based Therapies. Nat Rev Gene 12:329-340 (2011).
Dawson et al. Design, manufacture, and assay of the efficacy of siRNAs for gene silencing. Meth Mol Biol 439:403-419 (2008).
Drews et al. Drug discovery: a historical perspective. Science 287(5460):1960-1964 (2000).
Fakhrai et al. Eradication of Established Intracranial Rat Gliomas by Transforming Growth Factor β Antisense Gene Therapy. PNAS 93:2909-2914 (Apr. 1996).
Fakhrai et al. Phase I Clinical Trial of a TGF-β Antisense-Modified Tumor Cell Vaccine in Patients with Advanced Glioma. Cancer Gene Therapy 13:1052-1060 (2006).
Fire. Gene Silencing by Double-Stranded RNA (Nobel Lecture). Angew Chem Int Ed 46:6966-6984 (2007).
GenBank Accession BC012181 (4 pgs.) (2006).
GenBank Accession NM_002569.2 (5 pgs.) (2009).
Giering et al. Expression of shRNA From a Tissue-specific pol II Promoter Is an Effective and Safe RNAi Therapeutic. Mol Ther 16(9):1630-1636 (2008).
Gregory et al. Human RISC Couples MicroRNA Biogenesis and Posttranscriptional Gene Silencing. Cell 123:631-640 (2005).
Grimm et al. Fatality in Mice Due to Oversaturation of Cellular MicroRNA/Short Hairpin RNA Pathways. Nature 441:537-541 (2006).
Grimson et al. MicroRNA Targeting Specificity in Mammals:Determinants Beyond Seed Pairing. Molecular Cell 27:91-105 (2007).
Hofacker et al. Designing Optimal siRNA Based on Target Site Accessibility. Methods Mol Biol 623:137-157 (2010).
Homo sapiens furin (paired basic amino acid cleaving enzyme) (Furin), mRNA. NCBI Reference Sequence: NM_002569.2 http://www.ncbi.nlm.nih.gov/auccore/nm_002569.2 (7 pgs.) (Jan. 26, 2014).
Kim et al. Synthetic dsRNA Dicer substrates enhance RNAi potency and efficacy. Nat Biotechnol 23(2):222-226 (2005).
Kruhoffer et al. Isolation of microarray-grade total RNA, microRNA, and DNA from a single PAXgene blood RNA tube. J Mol Diagn 9(4):452-458 (2007).

(56) References Cited

OTHER PUBLICATIONS

Lovborg et al. Multiparametric evaluation of apoptosis: effects of standard cytotoxic agents and the cyanoguanidine CHC 828. Mol Cancer Ther 3(5):521-526 (2004).
Maples. A Novel Patient-Specific Cancer Vaccine Approach Based on Genetically Altered Tumor Immune Profile and Xenograft Tumor Expansion. Williamsburg BioProcessing Foundation's 12th International Cell & Tissue BioProcessing meeting held in Austin, Texas (Oct. 29-31, 2007) (15 pgs).
Mello. Return to the RNAi World: Rethinking Gene Expression and Evolution, Nobel Lecture. Cell Death Differ 14:2013-2020 (2007).
Moore et al. Short Hairpin RNA (shRNA): Design, Delivery, and Assessment of Gene Knockdown, Chapter 10. Methods in Molecular Biology 629:139-156 (2010).
Nemunaitis et al. A phase I trial of GMCSF gene-TGFbeta antisense gene autologous tumor cell (TAG) vaccine in advanced cancer. Mol Therapy 17(Suppl 1):S206 (2009).
Nemunaitis et al. Phase I trial of retroviral vector-mediated interferon (IFN)-gamma gene transfer into autologous tumor cells in patients with metastatic melanoma. Cancer Gene Therapy 5:292-300 (1998).
Nemunaitis et al. Phase II trial of Belagenpumatucel-L, a TGF-beta2 antisense gene modified allogeneic tumor vaccine in advanced non small cell lung cancer (NSCLC) patients. Cancer Gene Ther 16(8):620-624 (2009).
Nemunaitis. Vaccines in cancer: GVAX®, a GM-CSF gene vaccine. Expert Review of Vaccines 4:259-274 (2005).
PCT/US2010/061344 International Search Report and Written Opinion dated Feb. 20, 2011.
Phalon et al. Potential Use of RNA Interference in Cancer Therapy. Expert Rev Mol Med 12:e26 (Aug. 2010).
Preall et al. RNAi: RISC Gets Loaded. Cell 1213:543-553 (2005).
Roebroek et al. Limited Redundancy of the Proprotein Convertase Furin in Mouse Liver. J Biol Chem 279(51):53442-53450 (2004).
Simari et al. Requirements for Enhanced Transgene Expression by Untranslated Sequences from the Human Cytomegalovirus Immediate-Early Gene. Mol Med 4:700-706 (1998).
Siolas et al. Synthetic shRNAs as potent RNAi triggers. Nat Biotech 23(2):227-231 (2005).
Smith et al. Synergism between GM-CSF and IFNgamma: Enhanced immunotherapy in mice with glioma. Int J Cancer 120:75-80 (2007).
Sporn et al. Transforming growth factor-beta: biological function and chemical structure. Science 233(4763):532-534 (1986).
Templeton. Chapter 15: Liposomes for Gene Transfer in Cancer Therapy. Methods in Molecular Biology 651:271-278 (2010).
Templeton et al. Improved DNA: liposome complexes for increased systemic delivery and gene expression. Nat Biotechnol 15(7):647-652 (1997).
U.S. Appl. No. 12/973,787 Office Action dated Apr. 11, 2012.
U.S. Appl. No. 12/973,787 Office Action dated Apr. 29, 2014.
U.S. Appl. No. 12/973,787 Office Action dated Aug. 28, 2012.
U.S. Appl. No. 12/973,787 Office Action dated Nov. 25, 2013.
U.S. Appl. No. 12/973,787 Office Action dated Oct. 2, 2014.
U.S. Appl. No. 12/973,823 Office Action dated Apr. 7, 2014.
U.S. Appl. No. 12/973,823 Office Action dated Feb. 5, 2013.
U.S. Appl. No. 12/973,823 Office Action dated Oct. 23, 2014.
U.S. Appl. No. 12/973,823 Office Action dated Sep. 6, 2012.
U.S. Appl. No. 13/606,476 Office Action dated Apr. 7, 2014.
U.S. Appl. No. 13/606,476 Office Action dated Jun. 9, 2015.
U.S. Appl. No. 13/606,476 Office Action dated May 6, 2016.
U.S. Appl. No. 13/606,476 Office Action dated Oct. 13, 2015.
U.S. Appl. No. 13/606,476 Office Action dated Oct. 23, 2014.
U.S. Appl. No. 13/606,476 Office Action dated Sep. 22, 2016.
U.S. Appl. No. 14/815,721 Office Action dated Aug. 24, 2016.
U.S. Appl. No. 14/815,721 Office Action dated Mar. 28, 2016.
Verdine et al. The challenge of drugging undruggable targets in cancer: lessons learned from targeting BCL-2 family members. Clin Cancer Res. 13(24):7264-7270 (2007).
Walton et al. Designing Highly active siRNAs for Therapeutic Applications, Minireview. FEBS J 277:4806-4813 (2010).
Wang et al. RNA Interference and Cancer Therapy. Expert Review. Pharm Res 28(12):2983-2995 (2011).
Zhang et al. Removal of Endotoxin from Plasmid Solutions by Triton X-114 Phase Separation. Letters in Biotechnology 18(6):971-972 (2007) (English Abstract).
Zhou et al. A Tightly Regulated Pal III for Synthesis of miRNA Genes in Tandem. Biochimica et Biophysica Acta 1779:773-779 (2008).
Cicchelero et al. Various ways to improve whole cancer cell vaccines. Expert Review of Vaccines 13:721-735 (2014).
U.S. Appl. No. 14/815,721 Office Action dated Mar. 30, 2017.
Zaidi et al. The two faces of interferon-gamma in cancer. Clinical Cancer Research 17:6118-6124 (2011).

US 9,695,422 B2

FURIN-KNOCKDOWN BI-FUNCTIONAL RNA

CROSS-REFERENCE TO RELATED APPLICATIONS

This application claims priority to U.S. Provisional Application Ser. No. 61/289,661, filed Dec. 23, 2009, and is a Continuation of U.S. Ser. No. 12/973,787, filed Dec. 20, 2010, the entire contents of which is incorporated herein by reference.

TECHNICAL FIELD OF THE INVENTION

The present invention relates in general to the field of vaccine development, and more particularly, to the development of compositions and methods for making and using an autologous cancer vaccine genetically modified for Furin knockdown and GM-CSF expression.

STATEMENT OF FEDERALLY FUNDED RESEARCH

None.

REFERENCE TO A SEQUENCE LISTING

The present application includes a Sequence Listing filed separately in an electronic format as required by 37 C.F.R §1.821-1.825.

BACKGROUND OF THE INVENTION

Without limiting the scope of the invention, its background is described in connection with the development of genetically modified whole cell cancer vaccines. More specifically, the present invention relates to vaccines capable of augmenting tumor antigen expression, presentation, and processing through expression of the GM-CSF transgene and attenuating secretory immunosuppressive activity of TGF-β via furin bi-functional shRNA transgene induced knockdown.

The prevailing hypothesis for immune tolerance to cancer vaccines include the low immunogenicity of the tumor cells, the lack of appropriate presentation by professional antigen presenting cells, immune selection of antigen-loss variants, tumor induced immunosuppression, and tumor induced privileged site. Whole cancer cell vaccines can potentially solicit broad-based, polyvalent immune responses to both defined and undefined tumor antigens, thereby addressing the possibility of tumor resistance through downregulation and/or selection for antigen-loss variants. An example of a method for making a master cell bank of whole cell vaccines for the treatment of cancer can be found in U.S. Pat. No. 7,763,461 issued to Link et al. (2010). According to the '461 patent tumor cells are engineered to express an α (1,3) galactosyl epitope through ex-vivo gene therapy protocols. The cells are then irradiated or otherwise killed and administered to a patient. The α galactosyl epitope causes opsonization of the tumor cell enhancing uptake of the opsonized tumor cell by antigen presenting cells which results in enhanced tumor specific antigen presentation. The animal's immune system thus is stimulated to produce tumor specific cytotoxic cells and antibodies which will attack and kill tumor cells present in the animal Granulocyte-macrophage colony-stimulating factor, often abbreviated to GM-CSF, is a protein secreted by macrophages, T cells, mast cells, endothelial cells and fibroblasts. When integrated as a cytokine transgene, GM-CSF enhances presentation of cancer vaccine peptides, tumor cell lysates, or whole tumor cells from either autologous or established allogeneic tumor cell lines. GM-CSF induces the differentiation of hematopoietic precursors and attracts them to the site of vaccination. GM-CSF also functions as an adjuvant for dendritic cell maturation and activational processes. However, GM-CSF-mediated immunosensitization can be suppressed by tumor produced and/or secreted different isoforms of transforming growth factor beta (TGF-β). The TGF-β family of multifunctional proteins possesses well known immunosuppressive activities. The three known TGF-β ligands (TGF-β1, β2, and β3) are ubiquitous in human cancers. TGF-β overexpression correlates with tumor progression and poor prognosis. Elevated TGF-β levels within the tumor microenvironment are linked to an anergic antitumor response. TGF-β inhibits GM-CSF induced maturation of dendritic cells and their expression of MHC class II and co-stimulatory molecules. This negative impact of TGF-β on GM-CSF-mediated immune activation supports the rationale of depleting TGF-β secretion in GM-CSF-based cancer cell vaccines.

All mature isoforms of TGF-β require furin-mediated limited proteolytic cleavage for proper activity. Furin, a calcium-dependent serine endoprotease, is a member of the subtilisin-like proprotein convertase family. Furin is best known for the functional activation of TGF-β with corresponding immunoregulatory ramifications. Apart from the previously described immunosuppressive activities of tumor secreted TGF-β, conditional deletion of endogenously expressed furin in T lymphocytes has been found to allow for normal T-cell development, but impaired function of regulatory and effector T cells, which produced less TGF-β1. Furin expression by T cells appears to be indispensable in maintaining peripheral tolerance, which is due, at least in part, to its non-redundant, essential function in regulating TGF-β1 production.

High levels of furin have been demonstrated in virtually all cancer lines. The inventors and others have found that up to a 10-fold higher level of TGF-β1 may be produced by human colorectal, lung cancer, and melanoma cells, and likely impact the immune tolerance state by a higher magnitude. The presence of furin in tumor cells likely contributes significantly to the maintenance of tumor directed TGF-β peripheral immune tolerance. Hence furin knockdown (via RNA interference mechanism) represents a novel and attractive approach for optimizing GM-CSF-mediated immunosensitization. Vaccines based on the phenomenon of RNA interference (RNAi) have been previously described, for e.g. U.S. Patent Application No. 20040242518 (Chen et al. 2004) provides methods and compositions for inhibiting influenza infection and/or replication based on the phenomenon of RNAi as well as systems for identifying effective siRNAs and shRNAs for inhibiting influenza virus and systems for studying influenza virus infective mechanisms. The invention also provides methods and compositions for inhibiting infection, pathogenicity and/or replication of other infectious agents, particularly those that infect cells that are directly accessible from outside the body, e.g., skin cells or mucosal cells. In addition, the invention provides compositions comprising an RNAi-inducing entity, e.g., an siRNA, shRNA, or RNAi-inducing vector targeted to an influenza virus transcript and any of a variety of delivery agents. The invention further includes methods of use of the compositions for treatment of influenza Interferon-gamma (γIFN) is a key immunoregulatory cytokine that plays a critical role in the host innate and adaptive immune response and in tumor control. Also known as type II interferon, γIFN is a single-copy gene whose expression is regulated at multiple levels. γIFN coordinates a diverse array of cellular programs through transcriptional regulation of immunologically relevant genes. Initially, it was believed that CD4+ T helper cell type 1 (Th1) lymphocytes, CD8+ cytotoxic lymphocytes, and NK cells exclusively produced γIFN. However, there is now evidence that other cells, such as B cells, NKT cells, and professional antigen-presenting cells (APCs) secrete γIFN. γIFN production by professional APCs [monocyte/macrophage, dendritic cells (DCs)] acting locally may be important in cell self-activation and activation of nearby cells. γIFN secretion by NK cells and possibly professional APCs is likely to be important in early host defense against infection, whereas T lymphocytes become the major source of γIFN in the adaptive immune response. Furthermore, a role for γIFN in preventing development of primary and transplanted tumors has been identified. γIFN production is controlled by cytokines secreted by APCs, most notably interleukin (IL)-12 and IL-18. Negative regulators of γIFN production include IL-4, IL-10, glucocorticoids, and TGF-β.

SUMMARY OF THE INVENTION

The present invention includes a unique method of inhibiting TGF-β through RNA interference with furin, a proprotein convertase involved critically in the functional processing of all TGF-β isoforms. The FANG vector uniquely incorporates a bi-functional small hairpin construct (shRNA$^{furin}$) specific for the knockdown of furin. The bi-functional shRNA$^{furin}$ of the present invention comprises a two stem-loop structures with a miR-30a backbone. The first stem-loop structure is the siRNA component, while the second stem-loop structure is the miRNA-like component. The strategy is to use a single targeted site for both cleavage and sequestering mechanisms of RNA interference. The FANG construct contains GM-CSF and the bi-functional shRNA$^{furin}$ transcripts under the control of a mammalian promoter (CMV) that drives the entire cassette. This construct is used to generate an autologous (i.e., patient specific) cancer vaccine genetically modified for furin knockdown and GM-CSF expression.

The construct used to produce the FANG vaccine in the present invention includes a bi-functional shRNA$^{furin}$/GMCSF expression vector plasmid comprising two nucleic acid inserts. The first nucleic acid insert is operably linked to a promoter, and it encodes a Granulocyte Macrophage Colony Stimulating Factor (GM-CSF) cDNA. The second nucleic acid insert is also operably linked to the promoter, and it encodes one or more short hairpin RNAs (shRNA) capable of hybridizing to a region of an mRNA transcript encoding furin, thereby inhibiting furin expression via RNA interference. The bi-functional shRNA of the present invention has two mechanistic pathways of action, that of the siRNA and that of the miRNA. Thus, the bi-functional shRNA of the present invention is different from a traditional shRNA, i.e., a DNA transcription derived RNA acting by the siRNA mechanism of action or from a "doublet shRNA" that refers to two shRNAs, each acting against the expression of two different genes but in the traditional siRNA mode.

In one embodiment of the invention, the GM-CSF is human. The shRNA is bi-functional, incorporating both siRNA (cleavage dependent) and miRNA-like (cleavage-independent) motifs simultaneously. In one embodiment of the present invention, the shRNA is both the cleavage dependent and cleavage independent inhibitor of furin expression. The expression vector may contain a picornaviral 2A ribosomal skip peptide intercalated between the first and the second nucleic acid inserts, and the promoter may be CMV mammalian promoter which could contain a CMV IE 5' UTR enhancer sequence and a CMV IE Intron A. The mRNA sequences targeted by the bi-functional shRNA are not limited to the coding region of the furin mRNA transcript; in one embodiment, the shRNA may target the 3' untranslated region (UTR) sequence of the furin mRNA transcript.

The present invention also includes a vector that may be used to specifically knock down the expression of furin in target cells. This shRNA$^{furin}$ expression vector comprises a nucleic acid insert operably linked to a promoter. Such insert encodes one or more short hairpin RNAs (shRNA) capable of hybridizing to a region of an mRNA transcript encoding furin, thereby inhibiting furin expression via RNA interference. The bi-functional shRNA may simultaneously incorporate siRNA (cleavage dependent) and miRNA (cleavage-independent) motifs, and inhibit furin expression in both a cleavage dependent and cleavage independent manner. Additionally, the expression vector may target the coding region of the furin mRNA transcript, or in the alternative it may target the 3' UTR region sequence of the furin mRNA transcript.

The present invention further provides a composition comprising a therapeutically effective amount of cells with an expression vector. The expression of the composition comprises a cell transfected with a first nucleic acid insert operably linked to a promoter, wherein the first insert encodes GM-CSF and a second nucleic acid insert operably linked to the promoter, wherein the second insert encodes one or more short hairpin RNAs (shRNA) capable of hybridizing to a region of a mRNA transcript encoding furin, thereby inhibiting furin expression via RNA interference. In one aspect the GM-CSF is human. The encoded shRNA incorporates siRNA (cleavage dependent) and miRNA (cleavage-independent) motifs and functions as both a cleavage dependent and cleavage independent inhibitor of furin expression. The shRNA is further defined as a bi-functional shRNA.

A picornaviral 2A ribosomal skip peptide is intercalated between the first and the second nucleic acid inserts of the promoter, wherein the promoter is a CMV mammalian promoter, enhancer, and intron. The region targeted by the shRNA of the present invention is the 3' UTR region sequence of the furin mRNA transcript. Alternatively, the shRNA can also target the coding region of the furin mRNA transcript. As per the present invention the cells are autologous tumor cells, xenograft expanded autologous tumor cells or allogeneic tumor cells. In specific aspects of the present invention the cells are xenograft expanded allogeneic tumor cells and comprises $1\times10^7$ cells to $2.5\times10^7$ cells. The composition described herein further comprises a therapeutically effective dose of γIFN (gamma interferon), wherein the therapeutically effective dose of γIFN is 50 or 100 μg/m$^2$.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1A:
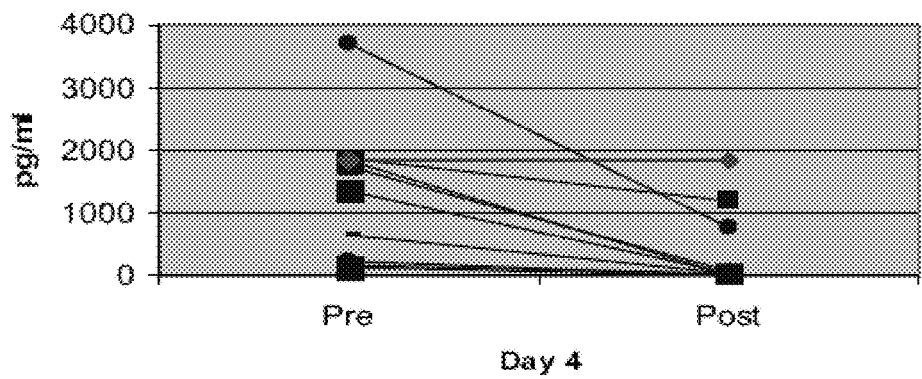
FIGS. 1A-1C show an assessment of GMCSF expression and TGF-β1 and -β2 knockdown, summarizing (FIG. 1A) TGF-β1, (FIG. 1B) TGF-β2, and (FIG. 1C) GM-CSF protein production before and after FANG or TAG (TAG 004) plasmid transfection. Values represent ELISA determinations of cytokine production in harvested autologous cancer cells transfected with FANG. Data represents autologus vaccines independently generated from 9 patients who underwent FANG processing (FANG 001-009). One patient had sufficient tissue to construct both a FANG (blue) and TAG vaccine (red) (FANG 004/TAG 004)

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein the term "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "expression vector" as used herein in the specification and the claims includes nucleic acid molecules encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter. The term "promoter" refers to any DNA sequence which, when associated with a structural gene in a host yeast cell, increases, for that structural gene, one or more of 1) transcription, 2) translation or 3) mRNA stability, compared to transcription, translation or mRNA stability (longer half-life of mRNA) in the absence of the promoter sequence, under appropriate growth conditions.

The term "oncogene" as used herein refers to genes that permit the formation and survival of malignant neoplastic cells (Bradshaw, T. K.: Mutagenesis 1, 91-97 (1986).

As used herein the term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

The term "hybridizing" refers to any process by which a strand of nucleic acid binds with a complementary strand through base pairing.

The term "transfection" refers to the introduction of foreign DNA into eukaryotic cells. Transfection may be accomplished by a variety of means known to the art including, e.g., calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein, the term "liposome" refers to a closed structure composed of lipid bilayers surrounding an internal aqueous space. The term "polycation" as used herein denotes a material having multiple cationic moieties, such as quaternary ammonium radicals, in the same molecule and includes the free bases as well as the pharmaceutically-acceptable salts thereof.

A list of some of the abbreviations used throughout the specification and the claims are listed herein below in Table 1.

TABLE 1

Abbreviations Table

| Abbreviation | Term |
|---|---|
| AE | Adverse event |
| ALT | Alanine transaminase (also referred to as SGPT) |
| ANC | Absolute neutrophil count |
| APC | Antigen Presenting Cells |
| AST | Aspartate transaminase (also referred to as SGOT) |
| BUN | Blood urea nitrogen |
| CBC | Complete blood count |
| CD | Cluster of differentiation |
| CMV | Cytomegalovirus |
| $CO_2$ | Total carbon dioxide |
| CR | Complete response |
| CRF | Case report form |
| CTCAE | Common Toxicity Criteria for Adverse Events |
| CTL | Cytotoxic T lymphocyte |
| DC | Dendritic cell(s) |
| DTH | Delayed-type hypersensitivity |
| ECOG PS | Eastern Cooperative Oncology Group Performance Score |
| ELISA | Enzyme-Linked ImmunoSorbent Assay |
| ELISPOT | Enzyme-Linked ImmunoSorbent Spot |
| ER | Endoplasmic reticulum |
| FANG | bishRNA$^{furin}$ and GMCSF Augmented Autologous Tumor Cell Vaccine |
| FL | Flt-3-Ligand |
| GM-CSF | Granulocyte Macrophage-Colony Stimulating Factor (Accession No. NM_000758) |
| GMP | Good manufacturing practice |
| GVAX | GMCSF Secreting autologous or allogenic tumor cells |
| HLA | Human Leukocyte Antigen |
| IBC | Institutional Biosafety Committee |
| IEC | Independent Ethics Committee |
| IL | Infiltrating lymphocytes |
| IRB | Institutional Review Board |
| LAK | Lymphokine-activated killer |
| LD | Longest diameter |
| LLC | Large latent complex |
| MHC | Major histocompatability complex |
| MLR | Mixed lymphocyte reaction |
| MR | Mannose receptor |
| NK | Natural Killer |
| NKT | Natural Killer T cell(s) |
| NSCLC | Non small cell lung cancer |
| PCR | Polymerase chain reaction |
| PD | Progressive disease |
| PI | Principal Investigator |
| PR | Partial response |
| PS | Performance Status |
| RECIST | Response Evaluation Criteria in Solid Tumors |
| SCLC | Small cell lung cancer |
| SD | Stable disease |
| SLC | Small latent complex |
| STMN1 | Stathmin 1 |
| TAP | transporter associated with Ag processing |
| TGF-β | Transforming growth factor-β |
| TIL | Tumor infiltrating lymphocytes |
| TNF | Tumor necrosis factor |
| ULN | Upper limits of normal |
| WNL | Within normal limits |

Furin is a member of the subtilisin-like proprotein convertase family. The members of this family are proprotein convertases (PCs) that process latent precursor proteins into their biologically active products. Furin, a calcium-dependent serine endoprotease, efficiently cleaves precursor proteins at their paired basic amino acid processing sites by the consensus sequence -Arg-X-K/Arg-Arg (RXK/RR), with -RXXR- (SEQ. ID NO: 1) constituting the minimal cleavage site. Like many other proteases, PCs are synthesized as inactive zymogens with an N-terminal prosegment extension, which is autocatalytically removed in the endoplasmic reticulum to achieve functionality.

High levels of furin have been demonstrated in virtually all cancer lines (Furin, Accession No. NM_002569, SEQ ID NO:2). A 10-fold higher level of TGF-β1 may be produced by human colorectal, lung cancer and melanoma cells, and likely impact the immune tolerance state by a higher magnitude. Transforming growth factors betas (TGF-β) are a family of multifunctional proteins with well known immunosuppressive activities. The three known TGF-β ligands (TGF-β1-3, Accession Nos. NM_000660, NM_003238, NM_003239.2, respectively) are ubiquitous in human cancers. TGF-β overexpression correlates with tumor progression and poor prognosis. Elevated TGF-β levels within the tumor microenvironment are linked to an anergic antitumor response. The presence of furin in tumor cells likely contributes significantly to the maintenance of tumor directed TGF-β1 peripheral immune tolerance. Hence, furin knockdown represents a novel and attractive approach for optimizing immunosensitization.

The incorporation of a bi-functional shRNA$^{furin}$ in combination with hGM-CSF into an autologous cell vaccine is demonstrated herein to promote and enhance the immune response based on its effect on the afferent limb of that immune response.

Other applications for the bi-functional shRNA$^{furin}$ include: (1) Systemic delivery via a tumor (±tumor extracellular matrix (ECM)) selective decorated (targeted), stealthed bilamellar invaginated liposome (BIV) to enhance the efferent limb of the immune response; (2) Systemic delivery via a tumor selective decorated (targeted), stealthed bilamellar invaginated liposome (BIV) to directly subvert the tumor promoting/maintaining effects of furin target molecules including, but not limited to, IGF-II, IGF-1R, PDGF A, and, in some tumor types, MT1-MMP; (3) Systemic delivery via a tumor selective decorated (targeted), stealthed bilamellar invaginated liposome (BIV) to directly subvert the NOTCH/p300 pathway in putative cancer stem cells; (4) Systemic delivery via a tumor selective decorated (targeted), stealthed bilamellar invaginated liposome (BIV) to inhibit activation of toxins associated with anthrax, Shiga, diphtheria, tetanus, botulism and Ebola and Marburg viruses and/or (5) Systemic and/or inhalational delivery of a bilamellar invaginated liposome (BIV) (±decoration and reversible masking/stealthing) to inhibit *Pseudomonas* exotoxin A production as an adjunct to antibiotic therapy in patients with diseases with heightened risk of *Pseudomonas* mediated morbidity and mortality, e.g., cystic fibrosis.

A Furin-knockdown and GM-CSF-augmented (FANG) Autologous Cancer Vaccine for Human Melanoma and Lung Cancer: FANG uniquely incorporates a proprietary bi-functional small hairpin RNA (shRNA) construct specific for the knockdown of furin, a proprotein convertase critically involved in the functional processing of all TGF-β isoforms. Prior work by the inventors has demonstrated the effectiveness of FANG in generating GM-C SF expression and TGF-β1 and -β2 depletion in human cancer lines.

As used herein the term "bi-functional" refers to a shRNA having two mechanistic pathways of action, that of the siRNA and that of the miRNA. The term "traditional" shRNA refers to a DNA transcription derived RNA acting by the siRNA mechanism of action. The term "doublet" shRNA refers to two shRNAs, each acting against the expression of two different genes but in the "traditional" siRNA mode.

Overcoming immune tolerance with cancer vaccines is a promising but difficult quest. The prevailing hypotheses for immune tolerance, based primarily on animal studies, include the low immunogenicity of the tumor cells, the lack of appropriate presentation by professional antigen presenting cells, immune selection of antigen-loss tumor variants, tumor induced immunosuppression, and tumor-induced privileged site [1]. Nevertheless, recent clinical trials that are based on transgene-expressing whole cancer cell vaccines have yielded promising results [2-5]. Whole cancer cell vaccines can potentially elicit broad-based, polyvalent immune responses to both defined and undefined tumor antigens, thereby addressing the possibility of tumor resistance through downregulation and/or selection for antigen-loss variants [6, 7].

Dranoff and Jaffee have shown in animal models [8], that tumor cells genetically modified to secrete GM-CSF, as compared to other cytokines, consistently demonstrated the most potent induction of anti-tumor immunity. When integrated as a cytokine transgene, GM-CSF enhances presentation of cancer vaccine peptides, tumor cell lysates, or whole tumor cells from either autologous or established allogeneic tumor cell lines [9]. GM-CSF induces the differentiation of hematopoietic precursors into professional antigen presenting (APC) dendritic cells (DC) and attracts them to the site of vaccination[8, 10]. GM-CSF also functions as an adjuvant for the DC maturation and activational processes of tumor antigen capture, process and presentation, upregulates their expression of costimulatory molecules, and their ability to migrate to secondary lymphoid tissues for activation of CD4+, CD8+ T cells, CD1d restricted invariant natural killer T (NKT) cells, and antibody producing B cells [11].

Recently, Hodi[12] reported that GVAX vaccination, followed by periodic infusions of anti-CTLA-4 antibodies to modulate effector and T regulatory cell functions, can generate clinically meaningful antitumor immunity in a majority of metastatic melanoma patients. These findings are consistent with the thesis that vaccination with a GM-CSF-augmented autologous cancer vaccine can successfully generate an immune mediated tumor destruction, particularly when coupled with an adjuvant treatment that depletes FoxP3+ Tregs activity, enhances tumor expression of MHC class I A chain (MICA) thereby activating natural killer (NK) and T cells, and enhances central memory T-cell CD4+ and CD8+ response.

TGF-β Knockdown: Transforming growth factors beta (TGF-β) are a family of multifunctional proteins with well known immunosuppressive activities [13]. The three known TGF-β ligands (TGF-β1, β2, and β3) are ubiquitous in human cancers. TGF-β overexpression correlates with tumor progression and poor prognosis [14, 15]. Elevated TGF-β levels within the tumor microenvironment are linked to an anergic antitumor response [14, 16-21]. TGF-β inhibits GM-CSF induced maturation of DCs [22] and their expression of MHC class II and co-stimulatory molecules [23]. Ardeshna [24] showed that lipopolysaccharide (LPS)-induced maturation of monocyte-derived DCs involved activation of p38 stress-activated protein kinase (p38SAPK), extracellular signal-regulated protein kinase (ERK), phosphoinositide 3-OH-kinase (PI3 kinase)/Akt, and nuclear factor (NF)-κB pathways. GM-CSF can exert parallel activities of stimulating myeloid hematopoietic cell and leukemia cell line proliferation through rapid, transient phosphorylation of MAP kinase 1/2 and ERK 1/2, whereas TGF-β turns off GM-CSF-induced ERK signaling via PI3-kinase-Akt pathway inhibition[25].

At the efferent level, antigen presentation by immature DCs contributes to T cell anergy [26]. TGF-β similarly inhibits macrophage activation[27] and their antigen presenting function[28, 29]. TGF-β inhibits the activation of cytotoxic T cells by impairing high affinity IL-2 receptor expression and function[30, 31]. TGF-β2 also converts naïve T cells to Treg cells by induction of the transcription factor FOXP3 [32], with emergence of Treg leading to the shutdown of immune activation[33]. According to Polak [34], tolerogenic DCs and suppressor T lymphocytes were present in all stages of melanoma. These immune cell types expressed TGF-β receptor I, and tolerogenic activity was dependent on TGF-β1 or -β2 binding.

At the innate immune response level, TGF-β is antagonistic on NK cells and down-regulates lymphokine activated killer (LAK) cell induction and proliferation[30, 35-39]. Penafuerte [40] recently showed that tumor-secreted TGF-β suppressed GM-CSF+IL2 (GIFT2) mediated immunosensitization of NK cells in the immunocompetent B16 melanoma model. In vivo blockade of B16 production of TGF-β improved survival otherwise compromised by the growth of non-GIFT2 expressing bystander tumors. These findings further validate the negative impact of TGF-β on GM-CSF-mediated immune activation in vivo, and by extension, support the rationale of depleting TGF-β secretion in GM-CSF-based cancer cell vaccines.

Trials conducted by the present inventors utilizing a tumor cell vaccine with TGF-β2 knockdown activity (Belagenpumatucel-L) in patients with non-small cell lung cancer demonstrated acceptable safety, and a dose-related survival improvement in response to randomized control patients and historical experience. The two-year survival for the late stage (IIIB/IV) patients was 52% for patients who received >2.5×10$^7$ cells/injection, which compares favorably with similar patient historical data of less than 10% survival at 2 years. The study patients also displayed significantly elevated cytokine production (IFN-γ, p=0.006; IL-6, p=0.004; IL4, p=0.007) and antibody titers to vaccine HLA antigens (p=0.014), suggesting an immune activating outcome. [41].

TGF-β-knockdown and GM-CSF Expressive Cancer Cell Vaccine (TAG): Thirty six patients were harvested for TAG vaccine. GM-CSF expression and TGF-β2 knockdown met product release criteria. Three (all gastrointestinal tumors with luminal access) had bacterial contaminants and could not be released. One had insufficient cells. Nineteen advanced refractory cancer patients were treated [42-44]. No Grade 3 toxic effects related to therapy were observed. Eleven of 17 (65%) evaluable patients maintained stable disease for at least 3 months. Thus the TAG vaccine appears to be safe and has evidence of clinical efficacy.

A potential limitation of TAG vaccine, however, is the restricted specificity for TGF-β2, given that all three known isoforms of TGF-β ligand (TGF-β1, -β2, and -β3) are ubiquitously produced in human cancers. In particular, up to a 10-fold higher level of TGF-β1 may be produced by human colorectal, lung cancer, and melanoma cells. The tolerogenic role of TGF-β1 in antigen presenting dendritic cells (DC) and T regulatory cells (Treg) is well established, and this activity is not impacted by TGF-β2 antisense treatment.

Furin: All mature isoforms of TGF-β require limited proteolytic cleavage for proper activity. The essential function of proteolytic activation of TGF-β is mediated by furin. Furin is a member of the subtilisin-like proprotein convertase family. The members of this family are proprotein convertases (PCs) that process latent precursor proteins into their biologically active products. Furin, a calcium-dependent serine endoprotease, efficiently cleaves precursor proteins at their paired basic amino acid processing sites by the consensus sequence -Arg-X-K/Arg-Arg (RXK/RR), with -RXXR- (SEQ. ID NO: 1) constituting the minimal cleavage site [53]. Like many other proteases, PCs are synthesized as inactive zymogens with an N-terminal prosegment extension, which is autocatalytically removed in the endoplasmic reticulum to achieve functionality [52].

Furin is best known for the functional activation of TGF-β with corresponding immunoregulatory ramifications [54, 55]. Apart from the previously described immunosuppressive activities of tumor secreted TGF-β, conditional deletion of endogenous-expressing furin in T lymphocytes was found to allow for normal T-cell development, but impaired the function of regulatory and effector T cells, which produced less TGF-β1. Furin-deficient Tregs were less protective in a T-cell transfer colitis model and failed to induce Foxp3 in normal T cells. Additionally, furin-deficient effector cells were inherently over-active and were resistant to suppressive activity of wild-type Treg cells. In APCs, cytotoxic T lymphocyte-sensitive epitopes in the trans-Golgi compartment were processed by furin and the less frequented TAP independent pathway [56]. Thus furin expression by T cells appears to be indispensable in maintaining peripheral tolerance, which is due, at least in part, to its non-redundant, essential function in regulating TGF-β1 production.

High levels of furin have been demonstrated in virtually all cancer lines [45-52]. The present inventors and others have found that up to a 10-fold higher level of TGF-β1 may be produced by human colorectal, lung cancer, and melanoma cells, and likely impact the immune tolerance state by a higher magnitude[34, 57, 58]. The presence of furin in tumor cells likely contributes significantly to the maintenance of tumor directed TGF-β1 peripheral immune tolerance [54]. Hence furin knockdown represents a novel and attractive approach for optimizing immunosensitization.

FANG (furin shRNA and GMCSF) vaccine: The present inventors constructed the next generation vaccine termed FANG. The novelty of the FANG vaccine lies in the combined approach of depleting multiple immunosuppressive TGF-β isoforms by furin knockdown, in order to maximize the immune enhancing effects of the incorporated GM-CSF transgene on autologous tumor antigen sensitization.

Figure 1B:
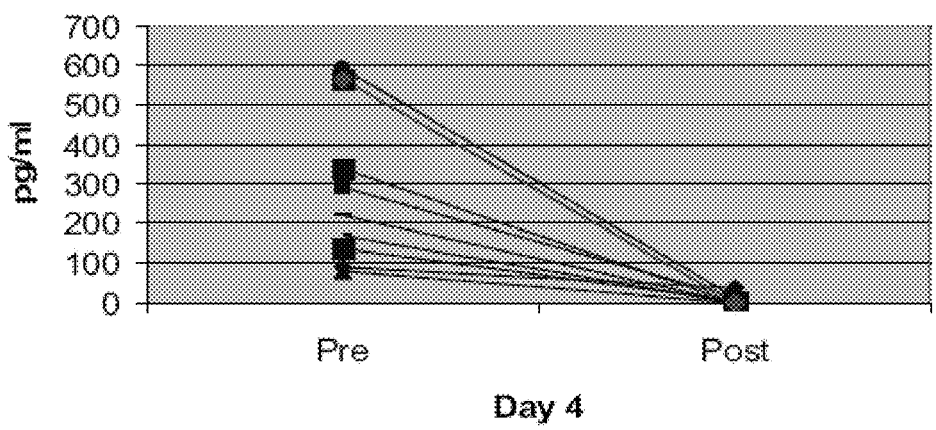
Figure 1C:
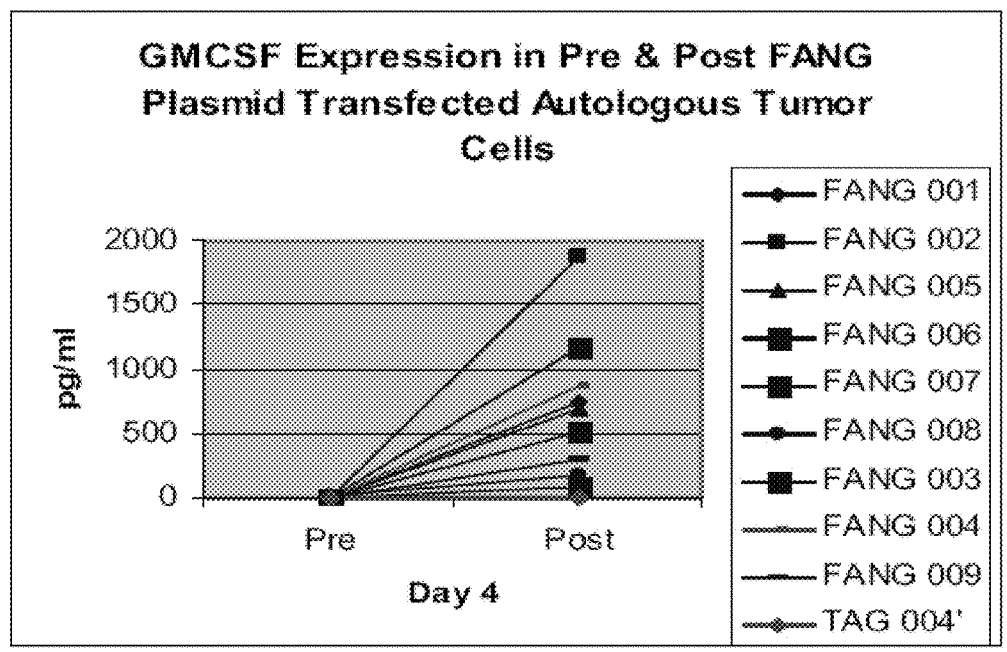

All mature isoforms of TGF-β require proteolytic activation by furin. The feasibility of achieving concomitant depletion of multiple TGF-β isoform activity in several cancer cell lines (H460, CCL-247, CRL-1585, U87) was determined using furin-knockdown and the present inventors have successfully completed GMP manufacturing of FANG vaccine in 9 cancer patients (breast—1; colon—2; melanoma—4; gallbladder—1; NSCLC—1). Assessment of GMCSF expression and TGF-β1 and -β2 knockdown is shown in FIGS. 1A-1C.

The capability of FANG to knockdown both TGF-β1 and -β2 is supported by findings in the first 9 patients (FIGS. 1A and 1B) who underwent vaccine construction. All 9 vaccine preparations demonstrated significantly elevated levels of GM-CSF (80-1870 pg/ml at day 4 of culture, median of 739 pg/ml). All 9 patients demonstrated >50% reductions of TGF-β2, and 6 of 7 patients with >100 pg of endogenous TGF-β1 production also demonstrated >50% reduction of this cytokine. The expanded target effectiveness of FANG is best demonstrated in one patient (NSCLC) who had adequate tumor tissue to generate both TAG (TAG-004A) and FANG (FANG-004) versions of autologous vaccine, TGF-β1 (as well as TGF-β2) was depleted to below detectable levels using the FANG preparation (FANG-004) from an initial concentration of 1840 pg/ml whereas this high level of TGF-β1 was unchanged with the TAG preparation (TAG-004) albeit with the expected depletion of TGF-β2. These findings support the potential advantage of the FANG vaccine preparation.

Validation of bioactivity of personalized cGMP FANG vaccines: Gene modification will be achieved by the use of a plasmid vector encoding for GM-CSF and a bi-functional short hairpin (bi-sh) RNA optimized for furin knockdown. Cancer patient autologous FANG vaccine has already been generated under cGMP conditions for clinical trial of patients with advanced solid cancers. GM-CSF and TGF-β1, -β2, and -β3 mRNA and protein expression were measured as part of the quality assurance process. Cytokine bioactivity following FANG modification was determined by growth outcome in a GM-CSF and TGF-β dependent cell line utilized by the present inventors in previous studies. Processed vaccine will undergo proteogenomic screening to verify antigenic integrity following FANG modification.

To characterize the augmenting effect of CTLA-4 blockade: Given that FANG immunization only impacts the afferent immunosensitization process, additional approaches that promote tumor-specific immune effector responses may further promote antitumor outcome. Disrupting Treg suppression and/or enhancing T effectors (Teff) by blockade of the cytotoxic T lymphocyte-4 (CTLA-4) function may enhance the likelihood of clinical success of the FANG vaccine.

Figure 2:
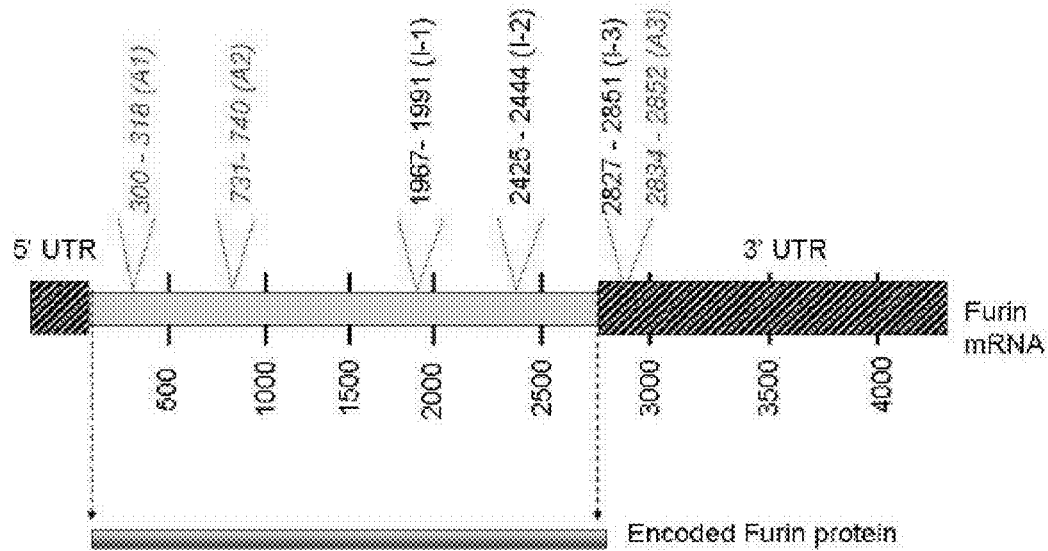
FIG. 2 shows the siRNA targeted regions of furin mRNA. Prospective siRNA targeting regions in 3'-UTR and encoding regions of furin mRNA and the targeted sequence by each siRNA.

The FANG approach was supported by the findings from 9 patient autologous vaccines, which consistently demonstrated TGF-β1 and TGF-β2 reductions and elevated GM-CSF levels (FIGS. 1A to 1C). Both TGF-β1 and TGF-β2 activity by specific immunoassay was also demonstrated to be significantly reduced in these cancer lines, confirming the effect of furin blockade on TGF-β isoform expression. The inventors validated the applicability of siRNA-mediated furin-knockdown for inhibiting TGF-β isoform expression. Prospective siRNA targeting sites (FIG. 2) in the furin mRNA sequence were determined by the published recommendations of Tuschl and colleagues and the additional selection parameters that integrated BLAST searches of the human and mouse genome databases (http:jura.wi.mit.edu/bioc/siRNAext). siRNAs targeting eligible translated and 3'UTRs sites (FIG. 2) were tested.

Following lipofection of CCL-247, CRL-1585 U87 and H460 cells, each of the 6 siRNA$^{furin}$ constructs was shown to markedly reduce TGF-β1 and TGF-β2 levels in culture supernatants without adversely affecting cell survival. Thus siRNA-mediated furin knockdown is effective for the depletion of TGF-β1 and -β2 isoforms.

Design and construction of FANG: A "bi-functional" vector was used that incorporates both siRNA and miRNA-like functional components for optimizing gene knockdown [61]. The siRNA component is encoded as a hairpin and encompasses complete matching sequences of the passenger and guide strands. Following cleavage of the passenger strand by the Argonaute-2 (Ago 2) of the RNA-induced silencing complex (RISC), an endonuclease with RNase H like activity, the guide strand binds to and cleaves the complementary target mRNA sequence (cleavage-dependent process). In distinction, the miRNA-like component of the "bi-functional" vector incorporates mismatches between the passenger and guide strands within the encoding shRNA hairpin in order to achieve lower thermodynamic stability. This configuration allows the passenger strand to dissociate from RISC without cleavage (cleavage-independent process) independent of Ago 2 [62, 63], and the miRNA guide component to downregulate its target through translational repression, mRNA degradation, and sequestration of the partially complementary target mRNA in the cytoplasmic processing bodies (P-body).

The inventors have previously demonstrated the enhanced effectiveness of a bi-functional shRNA to knockdown stathmin (STMN1; oncoprotein 18), a protein that regulates rapid microtubule remodeling of the cytoskeleton and found to be upregulated in a high proportion of patients with solid cancers [64]. The bi-functional shRNA construct achieved effective knockdown against STMN-1 resulting in a 5-log dose enhanced potency of tumor cell killing as compared with siRNA oligonucleotides directed against the same gene target.

A similarly designed bi-functional shRNA was used to effect furin knockdown. The bi-functional shRNA$^{furin}$ consists of two stem-loop structures with a miR-30a backbone; the first stem-loop structure has complete complementary guiding strand and passenger strand, while the second stem-loop structure has two by mismatches at positions 11 and 12 of the passenger strand. The inventors adopted a strategy of using a single targeted site for both cleavage and sequestration processes. The encoding shRNAs are proposed to allow mature shRNA to be loaded onto more than one type of RISC [65]. The inventors focused on a single site since multi-site targeting may increase the chance for "seed sequence" induced off-target effects [66].

The two stem-loop structure was put together with 10 pieces of complementing and interconnecting oligonucleotides through DNA ligation. Orientation of the inserted DNA was screened by PCR primer pairs designed to screen for the shRNA insert and orientation. Positive clones were selected and sequence confirmed at SeqWright, Inc. (Houston, Tex.). Based on siRNA findings, three bi-functional shRNA's were constructed. The optimal targeting sequence was identified.

The FANG construct has a single mammalian promoter (CMV) that drives the entire cassette, with an intervening 2A ribosomal skip peptide between the GM-C SF and the furin bi-functional shRNA transcripts, followed by a rabbit polyA tail. There is a stop codon at the end of the GM-CSF transcript.

Insertion of picornaviral 2A sequences into mRNAs causes ribosomes to skip formation of a peptide bond at the junction of the 2A and downstream sequences, leading to the production of two proteins from a single open reading frame [67]. The inventors found that the 2A linker to be effective for generating approximately equal levels of GM-CSF and anti-TGF-β transcripts with the TAG vaccine, and elected to use the same design for FANG.

cGMP FANG vaccines: Cancer patient autologous FANG vaccines were generated under cGMP conditions for use in clinical trials. GM-CSF and TGF-β1, -β2, and -β3 mRNA and protein expression were measured before and after FANG modification, and cytokine bioactivity determined by growth outcome on a GM-CSF and TGF-β dependent human cell line we have previously characterized. Each patient's processed vaccine will undergo proteogenomic screening to verify antigenic integrity following FANG modification.

cGMP production of FANG: FANG vaccine was generated by plasmid vector electroporation of established human cell lines. The selected FANG plasmid vector represents a construct containing the furin shRNA that has been prevalidated for optimal TGF-β downregulation.

Quantification of GM-CSF and TGF-β expressions: GM-CSF and TGF-β1 and -β2 expression was determined by cytokine specific colorimetric assay [68].

Validation of bioactivity: GM-CSF-induced proliferative activity similar to that of myeloid hematopoietic cells has been observed in myeloid leukemia cell lines, as mediated by the rapid and transient phosphorylation of MAP kinase 1/2 and ERK 1/2. By contrast, TGF-β turns off GM-CSF-mediated ERK signaling by inhibition of the PI3-kinase-Akt pathway [25]. The growth regulatory effects of GM-CSF and TGF-β on myeloid leukemic cells were used as an in vitro surrogate model to validate cytokine bioactivity in prepared FANG vaccine culture supernatants.

Cytokine activities in the FANG (or control-transfected) vaccine culture supernatants were validated by co-culture studies with erythroleukemic CD34+TF-1a cells [69] and, if necessary, confirmed with the biphenotypic B myelomonocytic leukemic CD10+CD15+MV4-11 cells [70] (ATCC, Rockville, Md.). Both of these cell lines have been shown respond to the positive proliferative effects of GM-CSF and the negative inhibitory activity of TGF-β at ng/ml amounts [25]. Proliferative activity will be determined by Easycount Viasure assay (Immunicon) and MTT assay [68].

Phenotypic profile analysis of FANG modification: Furin knockdown likely impacts the expression of other protein substrates with the target sequence in addition to TGF-β downregulation[51]. The antigenic profile of the FANG-processed autologous vaccines were determined from cancer patients, in the event that this information may be useful towards the understanding any differential clinical outcome in vaccinated patients.

High throughput genetic profiling was used to develop individualized therapeutics for cancer patients. High throughput, gene expression array analysis was carried out to compare the differential gene expression profile of FANG-transfected vs. control vector-transfected cancer cells.

Differentially labeled FANG and control preparations are combined and fractionated by high performance liquid chromatography (Dionex), using a strong cation exchange column (SCX) and a $2^{nd}$ dimension RP nano column. The fractions are spotted onto Opti-TOF™ LC/MALDI Insert (123×81 mm) plates (Applied Biosystems) in preparation for mass spectrometry analysis using the Applied Biosystems 4800 MALDI TOF/TOF™ Analyzer. Both protein and gene expression data were then evaluated by the GeneGo, Meta-Core software suite.

Proteogenomic analysis was carried out for the purpose of determining the antigen repertoire of the autologous cancer vaccine before and after FANG process. In addition to the validation of furin knockdown, particular attention was focused on 1) baseline and differential expression of furin-substrate proteins; 2) expression of landmark tumor-associated antigens (TAAs; such as gp100, Mart1, MAGE-1, tyrosinase, for melanoma; MAGE-3, MUC-1 for non-small cell lung cancer) [71, 72] and other reported TAAs; 3) HLA antigens and co-stimulatory molecules (CD80/86) expression; 4) proteins unrelated to the above categories that are differentially expressed by 2-fold or higher following FANG transfection.

Figure 3:
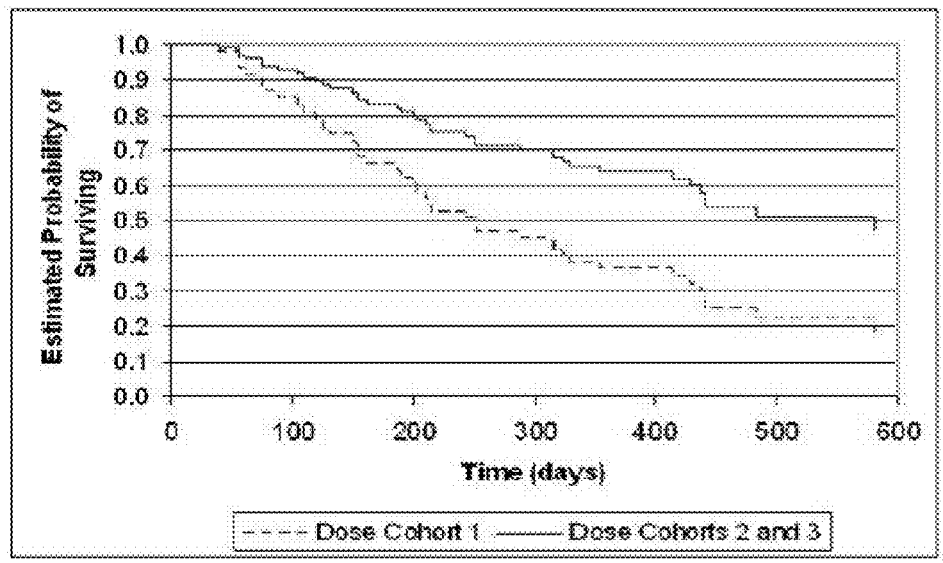
FIG. 3 shows the overall survival for Cohort 1 versus Cohorts 2 and 3 for advanced-stage patients (n=61; P=0.0186)
Figure 4:
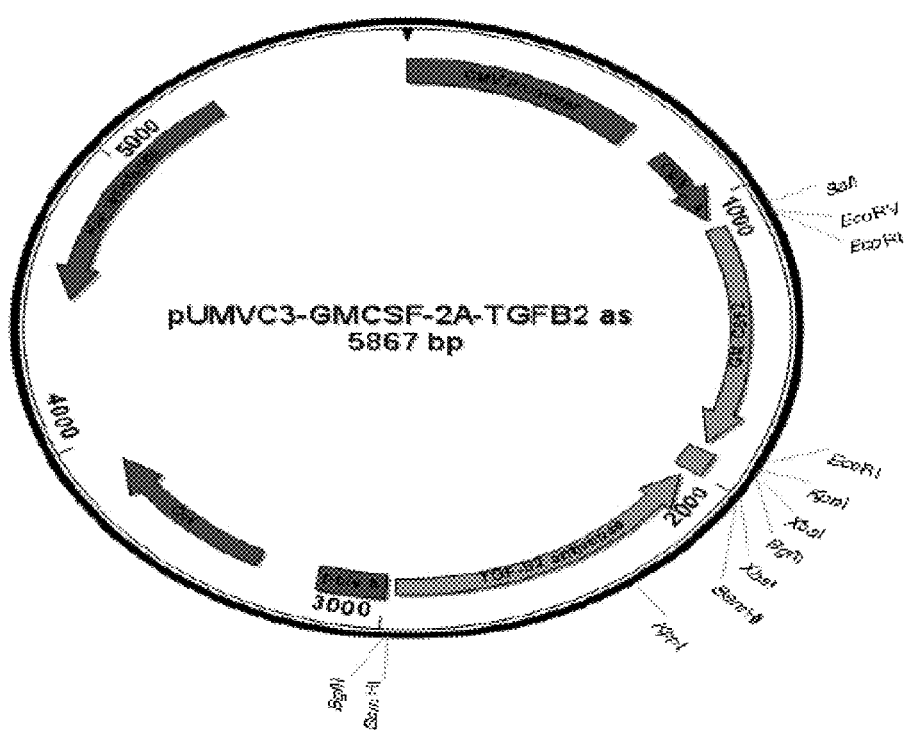
FIG. 4 shows a schematic diagram of GM-CSF-TGF-β2 antisense plasmid.
Figure 5:
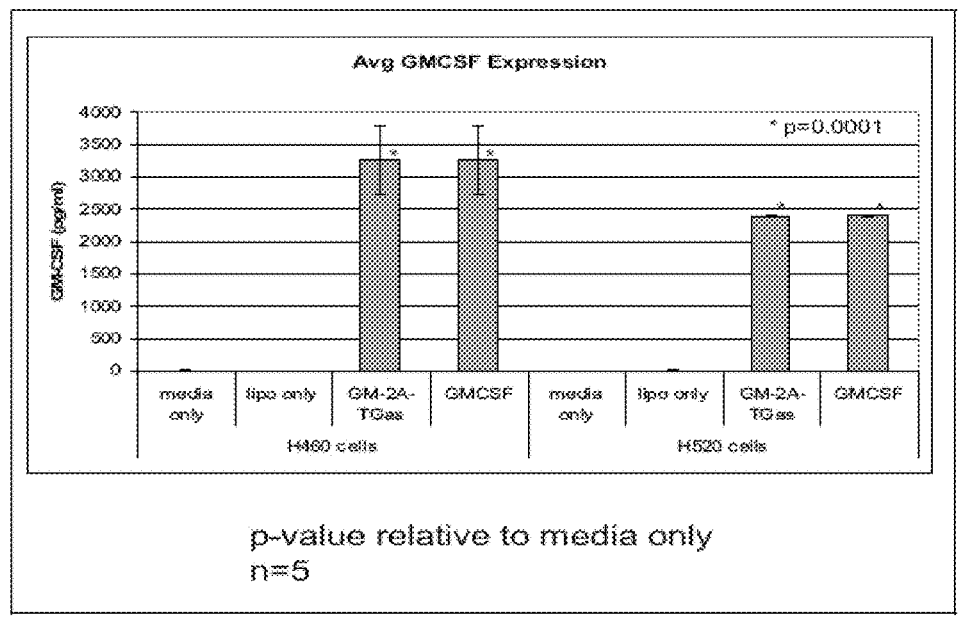
FIG. 5 shows the expression of GM-CSF in NCI-H-460 Squamous Cell and NCI-H-520, Large Cell (NSCLC) containing the pUMVC3-GM-CSF-2A-TGF-β2 antisense vector, in vitro.

In FIG. 3 the overall survival for Cohort 1 versus Cohorts 2 and 3 for advanced-stage patients (n=61; P=0.0186) is shown. A schematic diagram of GM-CSF-TGF-β2 antisense plasmid is represented by FIG. 4. The expression of GM-CSF in NCI-H-460 Squamous Cell and NCI-H-520, Large Cell (NSCLC) containing the pUMVC3-GM-CSF-2A-TGF-β2 antisense vector, in vitro is depicted in FIG. 5.

Figure 6:
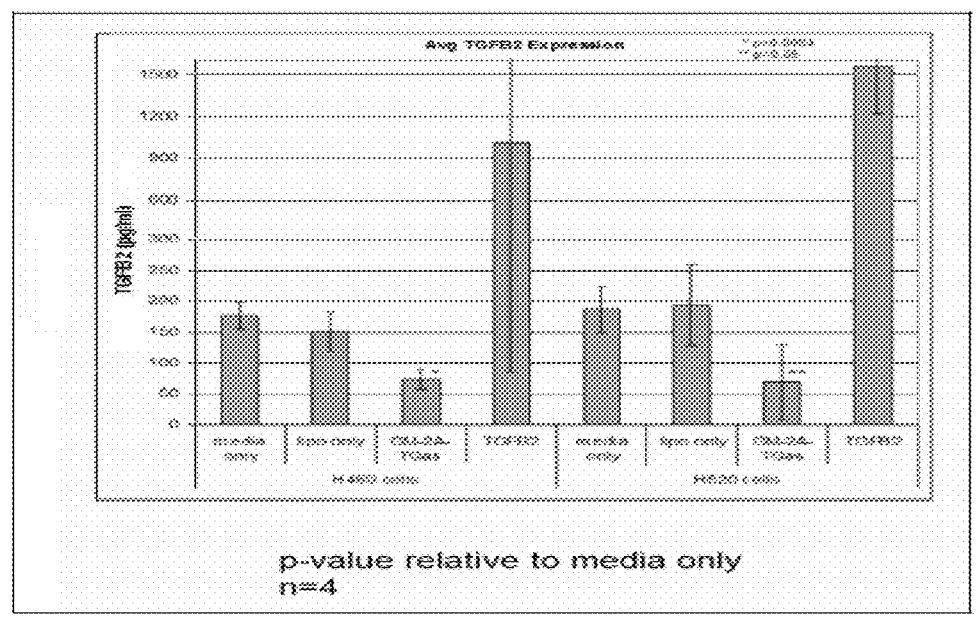
FIG. 6 shows that TGF-β2 levels are reduced in NCI-H-460 Squamous Cell and NCI-H-520, Large Cell (NSCLC) with the pUMVC3-GM-CSF-2A-TGF-β2 antisense vector.
Figure 7:
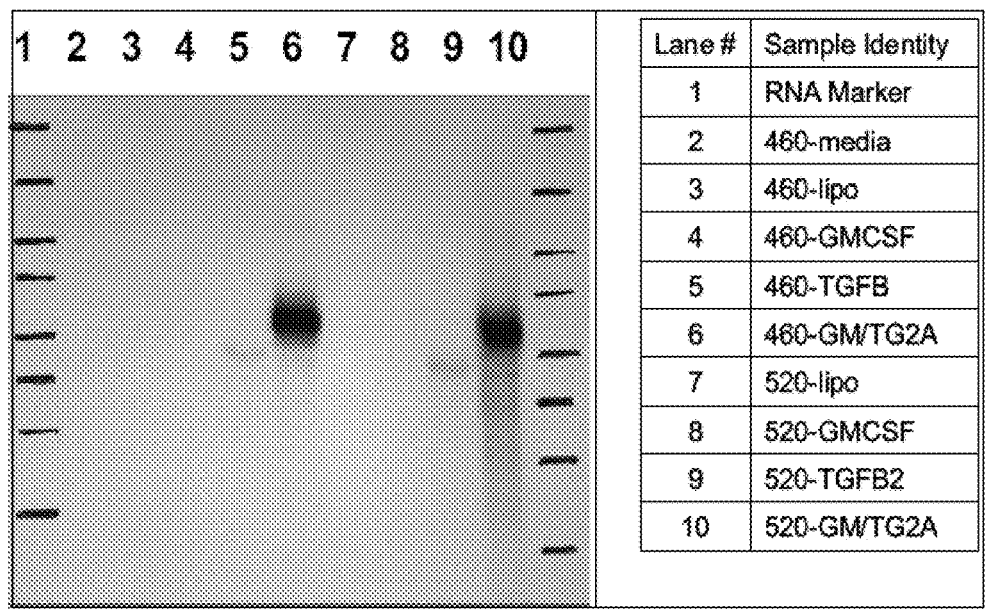
FIG. 7 shows that a 251 base pair probe specifically detects the GM-CSF-2A-TGF-β2 transcript expressed in vitro in NCI-H-460 and NCI-H-520 cells (lanes 6 and 10)
Figure 8:
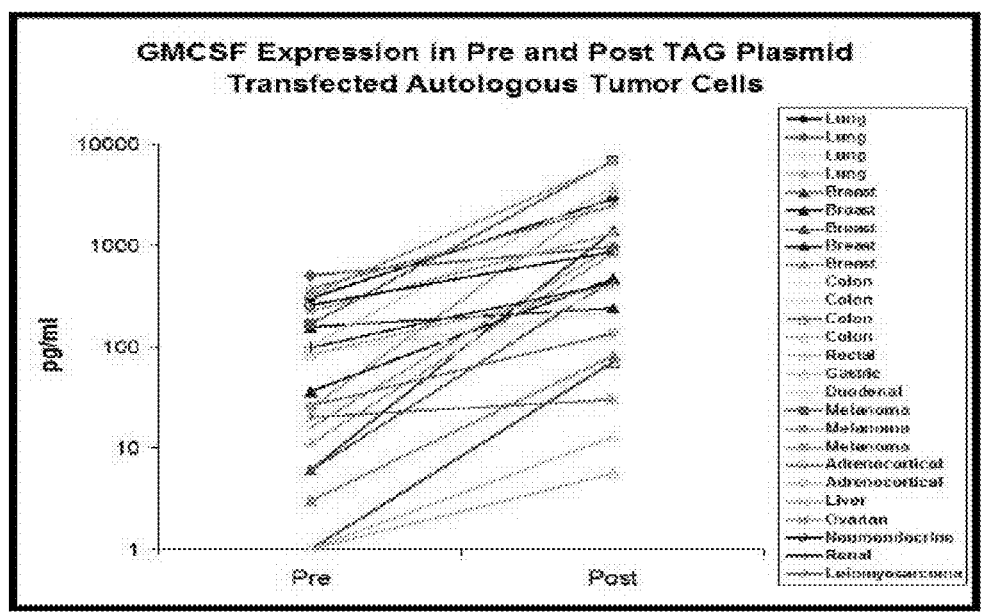
FIG. 8 shows the GM-CSF expression in TAG vaccines.
Figure 9:
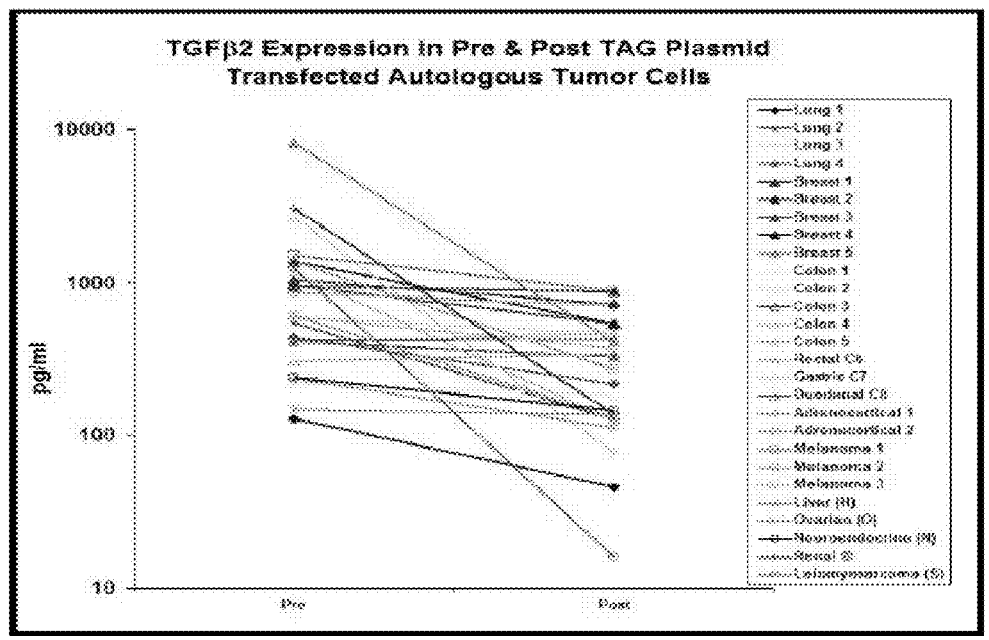
FIG. 9 shows the TGF-β2 expression in TAG vaccines.

Data presented in FIG. 6 shows the reduction in TGF-β2 levels in NCI-H-460 Squamous Cell and NCI-H-520, Large Cell (NSCLC) with the pUMVC3-GM-CSF-2A-TGF-β2 antisense vector. FIG. 7 shows that a 251 base pair probe specifically detects the GM-CSF-2A-TGF-β2 transcript expressed in vitro in NCI-H-460 and NCI-H-520 cells (lanes 6 and 10). FIGS. 8 and 9 shows the GM-CSF and TGF-β2 expression in TAG vaccines, respectively.

Figure 10A:
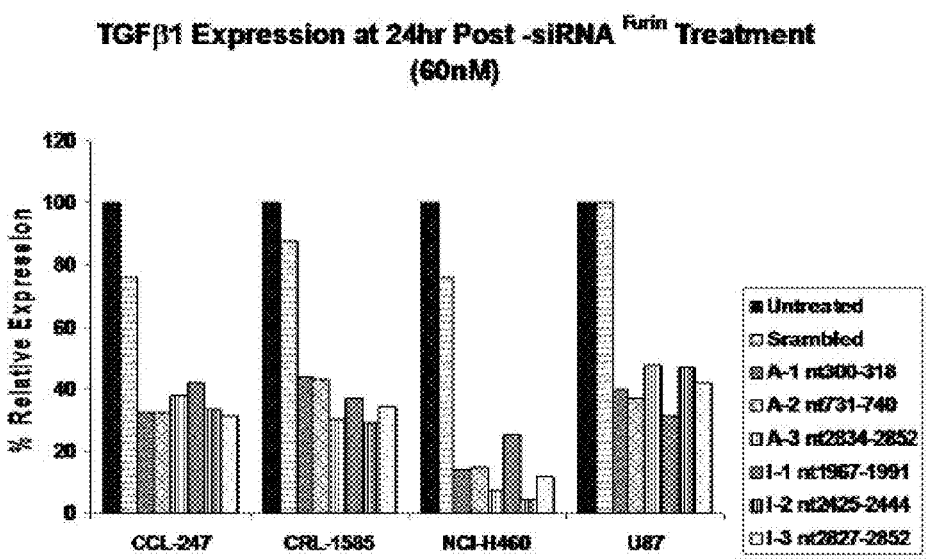
FIGS. 10A and 10B show expression of (FIG. 10A) TGF-β1 and (FIG. 10B) TGF-β2 in human cancer lines following siRNAfurin knockdown.
Figure 10B:
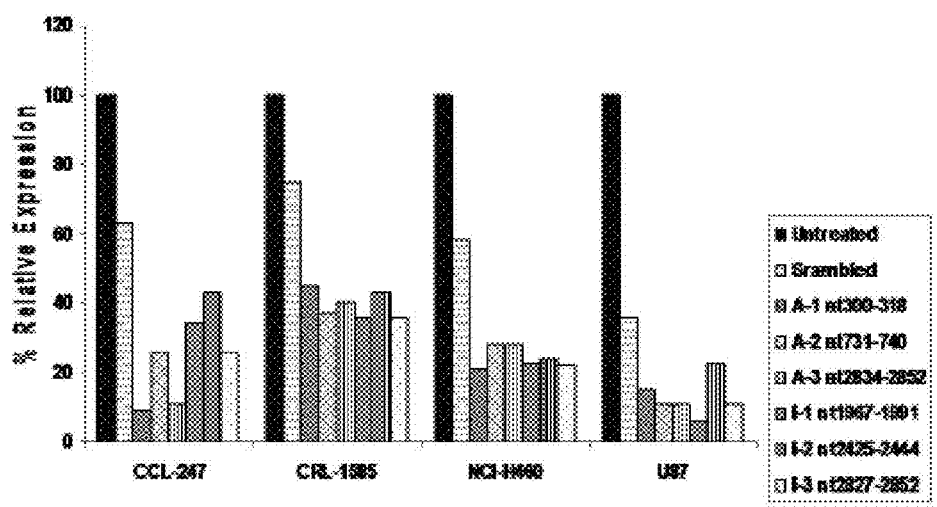
Figure 11:
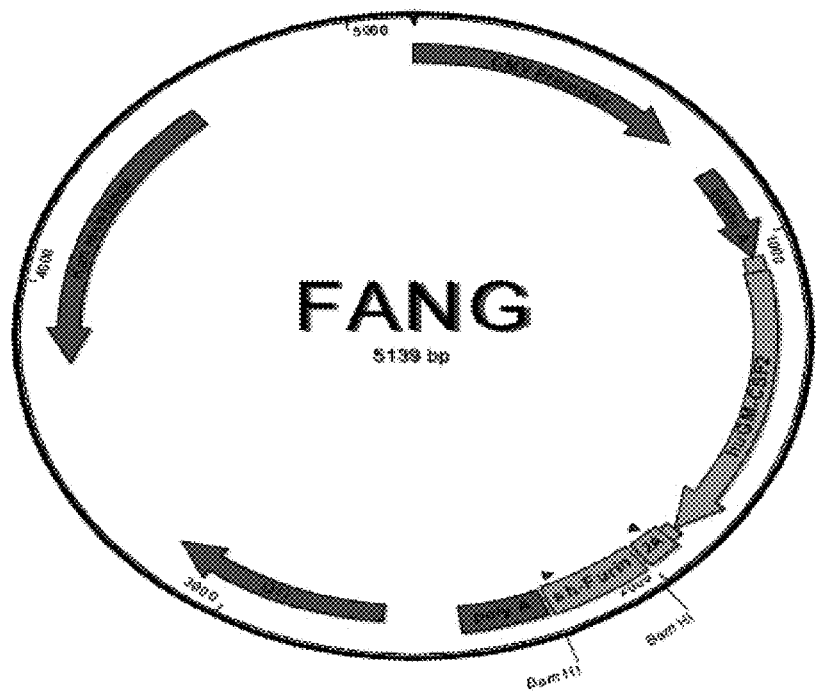
FIG. 11 shows the plasmid construct of FANG.

FIG. 10A shows the expression TGF-β1 in human cancer lines following siRNA$^{furin}$ knockdown. Similar expression profile for TGF-β2 is shown in FIG. 10B. FIG. 11 shows the plasmid construct of FANG It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 7,763,461: Antitumor vaccination using allogeneic tumor cells expressing alpha (1,3)-galactosyl transferase.

U.S. patent application Ser. No. 20040242518: Influenza therapeutic.

1. Murphy, K., Travers, P., Walport, M., ed. Janeway's Immunobiology. 7th ed. 2008, Garland Science: New York. 674-687.

2. Fakhrai, H., et al., Phase I clinical trial of a TGF-beta antisense-modified tumor cell vaccine in patients with advanced glioma. Cancer Gene Ther, 2006. 13(12): p. 1052-60.

3. Nemunaitis, J., GVAX (GMCSF gene modified tumor vaccine) in advanced stage non small cell lung cancer. J Control Release, 2003. 91(1-2): p. 225-31.

4. Nemunaitis, J., et al., Phase 1/2 trial of autologous tumor mixed with an allogeneic GVAX vaccine in advanced-stage non-small-cell lung cancer. Cancer Gene Ther, 2006. 13(6): p. 555-62.

5. Nemunaitis, J. and J. Nemunaitis, A review of vaccine clinical trials for non-small cell lung cancer. Expert Opin Biol Ther, 2007. 7(1): p. 89-102.

6. Ahmad, M., R. C. Rees, and S. A. Ali, Escape from immunotherapy: possible mechanisms that influence tumor regression/progression. Cancer Immunol Immunother, 2004. 53(10): p. 844-54.

7. Hege, K. M., K. Jooss, and D. Pardoll, GM-CSF gene-modifed cancer cell immunotherapies: of mice and men. Int Rev Immunol, 2006. 25(5-6): p. 321-52.

8. Dranoff, G., et al., Vaccination with irradiated tumor cells engineered to secrete murine granulocyte-macrophage colony-stimulating factor stimulates potent, specific, and long-lasting anti-tumor immunity. Proc Natl Acad Sci USA, 1993. 90(8): p. 3539-43.

9. Hege, K. M. and D. P. Carbone, Lung cancer vaccines and gene therapy. Lung Cancer, 2003. 41 Suppl 1: p. S103-13.

10. Huang, A. Y., et al., Role of bone marrow-derived cells in presenting MHC class I-restricted tumor antigens. Science, 1994. 264(5161): p. 961-5.

11. Banchereau, J., et al., Immunobiology of dendritic cells. Annu Rev Immunol, 2000. 18: p. 767-811.

12. Hodi, F. S., et al., Immunologic and clinical effects of antibody blockade of cytotoxic T lymphocyte-associated antigen 4 in previously vaccinated cancer patients. Proc Natl Acad Sci USA, 2008. 105(8): p. 3005-10.

13. Wick, W., U. Naumann, and M. Weller, Transforming growth factor-beta: a molecular target for the future therapy of glioblastoma. Curr Pharm Des, 2006. 12(3): p. 341-9.

14. Bierie, B. and H. L. Moses, Tumour microenvironment: TGFbeta: the molecular Jekyll and Hyde of cancer. Nat Rev Cancer, 2006. 6(7): p. 506-20.

15. Levy, L. and C. S. Hill, Alterations in components of the TGF-beta superfamily signaling pathways in human cancer. Cytokine Growth Factor Rev, 2006. 17(1-2): p. 41-58.

16. Sporn, M. B., et al., Transforming growth factor-beta: biological function and chemical structure. Science, 1986. 233(4763): p. 532-4.

17. Massague, J., The TGF-beta family of growth and differentiation factors. Cell, 1987. 49(4): p. 437-8.

18. Bodmer, S., et al., Immunosuppression and transforming growth factor-beta in glioblastoma. Preferential production of transforming growth factor-beta 2. J Immunol, 1989. 143(10): p. 3222-9.

19. Border, W. A. and E. Ruoslahti, Transforming growth factor-beta in disease: the dark side of tissue repair. J Clin Invest, 1992. 90(1): p. 1-7.

20. Chen, T. C., et al., TGF-B2 and soluble p55 TNFR modulate VCAM-1 expression in glioma cells and brain derived endothelial cells. J Neuroimmunol, 1997. 73(1-2): p. 155-61.

21. Li, M. O., et al., Transforming growth factor-beta regulation of immune responses Annu Rev Immunol, 2006. 24: p. 99-146.

22. Yamaguchi, Y., et al., Contrasting effects of TGF-beta 1 and TNF-alpha on the development of dendritic cells from progenitors in mouse bone marrow. Stem Cells, 1997. 15(2): p. 144-53.

23. Geissmann, F., et al., TGF-beta 1 prevents the non-cognate maturation of human dendritic Langerhans cells. J Immunol, 1999. 162(8): p. 4567-75.

24. Ardeshna, K. M., et al., The PI3 kinase, p38 SAP kinase, and NF-kappaB signal transduction pathways are involved in the survival and maturation of lipopolysaccharide-stimulated human monocyte-derived dendritic cells. Blood, 2000. 96(3): p. 1039-46.

25. Montenegro, D. E., et al., TGFbeta inhibits GM-CSF-induced phosphorylation of ERK and MEK in human myeloid leukaemia cell lines via inhibition of phosphatidylinositol 3-kinase (PI3-k). Cell Prolif, 2009. 42(1): p. 1-9.

26. Steinman, R. M., et al., Dendritic cell function in vivo during the steady state: a role in peripheral tolerance. Ann N Y Acad Sci, 2003. 987: p. 15-25.

27. Ashcroft, G. S., Bidirectional regulation of macrophage function by TGF-beta. Microbes Infect, 1999. 1(15): p. 1275-82.

28. Du, C. and S. Sriram, Mechanism of inhibition of LPS-induced IL-12p40 production by IL-10 and TGF-beta in ANA-1 cells. J Leukoc Biol, 1998. 64(1): p. 92-7.

29. Takeuchi, M., P. Alard, and J. W. Streilein, TGF-beta promotes immune deviation by altering accessory signals of antigen-presenting cells. J Immunol, 1998. 160(4): p. 1589-97.

30. Ruffini, P. A., et al., Factors, including transforming growth factor beta, released in the glioblastoma residual cavity, impair activity of adherent lymphokine-activated killer cells. Cancer Immunol Immunother, 1993. 36(6): p. 409-16.

31. Fakhrai, H., et al., Eradication of established intracranial rat gliomas by transforming growth factor beta antisense gene therapy. Proc Natl Acad Sci USA, 1996. 93(7): p. 2909-14.

32. Fantini, M. C., et al., Cutting edge: TGF-beta induces a regulatory phenotype in CD4+CD25− T cells through Foxp3 induction and down-regulation of Smad7. J Immunol, 2004. 172(9): p. 5149-53.

33. Thomas, D. A. and J. Massague, TGF-beta directly targets cytotoxic T cell functions during tumor evasion of immune surveillance. Cancer Cell, 2005. 8(5): p. 369-80.

34. Polak, M. E., et al., Mechanisms of local immunosuppression in cutaneous melanoma. Br J Cancer, 2007. 96(12): p. 1879-87.

35. Rook, A. H., et al., Effects of transforming growth factor beta on the functions of natural killer cells: depressed cytolytic activity and blunting of interferon responsiveness. J Immunol, 1986. 136(10): p. 3916-20.

36. Kasid, A., G. I. Bell, and E. P. Director, Effects of transforming growth factor-beta on human lymphokine-activated killer cell precursors. Autocrine inhibition of cellular proliferation and differentiation to immune killer cells. J Immunol, 1988. 141(2): p. 690-8.

37. Tsunawaki, S., et al., Deactivation of macrophages by transforming growth factor-beta. Nature, 1988. 334(6179): p. 260-2.

38. Hirte, H. and D. A. Clark, Generation of lymphokine-activated killer cells in human ovarian carcinoma ascitic fluid: identification of transforming growth factor-beta as a suppressive factor. Cancer Immunol Immunother, 1991. 32(5): p. 296-302.

39. Naganuma, H., et al., Transforming growth factor-beta inhibits interferon-gamma secretion by lymphokine-activated killer cells stimulated with tumor cells. Neurol Med Chir (Tokyo), 1996. 36(11): p. 789-95.

40. Penafuerte, C. and J. Galipeau, TGF beta secreted by B16 melanoma antagonizes cancer gene immunotherapy bystander effect. Cancer Immunol Immunother, 2008. 57(8): p. 1197-206.

41. Nemunaitis, J., et al., Phase II trial of Belagenpumatucel-L, a TGF-beta2 antisense gene modified allogeneic tumor vaccine in advanced non small cell lung cancer (NSCLC) patients. Cancer Gene Ther, 2009. 16(8): p. 620-4.

42. Maples P B, K. P., Oxendine I, Jay C, Yu Y, Kuhn J, Nemunaitis J, TAG Vaccine: Autologous Tumor Vaccine Genetically Modified to Express GM-CSF and Block Production of TGFB2. BioProcessing Journal, 2009. 8(2).

43. Nemunaitis, J., Kumar, P., Senzer, N., Yu, Y., Oxendine, I., Tong, A. W., Maples, P. B., A phase I trial of 43. GMCSF gene-TGFbeta antisense gene autologous tumor cell (TAG) vaccine in advanced cancer. Mol Therapy, 2009. 17 (Suppl 1): p. S206.

44. Maples, P. B., et al. Autologous Tumor Cell Vaccine Genetically Modified To Express GM-CSF and Block Expression of TGFb2 (Abstract #553). in The Twelfth Annual Meeting of the American Society of Gene Therapy. 2009. San Diego, Calif.

45. Page, R. E., et al., Increased expression of the proprotein convertase furin predicts decreased survival in ovarian cancer. Cell Oncol, 2007. 29(4): p. 289-99.

46. Schalken, J. A., et al., fur gene expression as a discriminating marker for small cell and nonsmall cell lung carcinomas. J Clin Invest, 1987. 80(6): p. 1545-9.

47. Mbikay, M., et al., Comparative analysis of expression of the proprotein convertases furin, PACE4, PC1 and PC2 in human lung tumours. Br J Cancer, 1997. 75(10): p. 1509-14.

48. Cheng, M., et al., Pro-protein convertase gene expression in human breast cancer. Int J Cancer, 1997. 71(6): p. 966-71.

49. Bassi, D. E., H. Mahloogi, and A. J. Klein-Szanto, The proprotein convertases furin and PACE4 play a significant role in tumor progression. Mol Carcinog, 2000. 28(2): p. 63-9.

50. Bassi, D. E., et al., Elevated furin expression in aggressive human head and neck tumors and tumor cell lines. Mol Carcinog, 2001. 31(4): p. 224-32.

51. Lopez de Cicco, R., et al., Human carcinoma cell growth and invasiveness is impaired by the propeptide of the ubiquitous proprotein convertase furin. Cancer Res, 2005. 65(10): p. 4162-71.

52. Khatib, A. M., et al., Proprotein convertases in tumor progression and malignancy: novel targets in cancer therapy. Am J Pathol, 2002. 160(6): p. 1921-35.

53. Thomas, G., Furin at the cutting edge: from protein traffic to embryogenesis and disease. Nat Rev Mol Cell Biol, 2002. 3(10): p. 753-66.

54. Pesu, M., et al., T-cell-expressed proprotein convertase furin is essential for maintenance of peripheral immune tolerance. Nature, 2008. 455(7210): p. 246-50.

55. Pesu, M., et al., Proprotein convertase furin is preferentially expressed in T helper 1 cells and regulates interferon gamma. Blood, 2006. 108(3): p. 983-5.

56. Lu, J., et al., TAP-independent presentation of CTL epitopes by Trojan antigens. J Immunol, 2001. 166(12): p. 7063-71.

57. Fogel-Petrovic, M., et al., Physiological concentrations of transforming growth factor beta1 selectively inhibit human dendritic cell function. Int Immunopharmacol, 2007. 7(14): p. 1924-33.

58. Bommireddy, R. and T. Doetschman, TGFbeta1 and Treg cells: alliance for tolerance. Trends Mol Med, 2007. 13(11): p. 492-501.

59. Henrich, S., et al., The crystal structure of the proprotein processing proteinase furin explains its stringent specificity. Nat Struct Biol, 2003. 10(7): p. 520-6.

60. Pearton, D. J., et al., Proprotein convertase expression and localization in epidermis: evidence for multiple roles and substrates. Exp Dermatol, 2001. 10(3): p. 193-203.

61. Rao, D., Maples, P. B., Senzer, N., Kumar, P., Wang, Z., papper, B. O., Yu, Y., Haddock, C., Tong, A., Nemunaitis, J., Bi-functional shRNA: A novel approach of RNA interference. (submitted), 2009.

62. Matranga, C., et al., Passenger-strand cleavage facilitates assembly of siRNA into Ago2-containing RNAi enzyme complexes. Cell, 2005. 123(4): p. 607-20.

63. Leuschner, P. J., et al., Cleavage of the siRNA passenger strand during RISC assembly in human cells. EMBO Rep, 2006. 7(3): p. 314-20.

64. Rana, S., et al., Stathmin 1: a novel therapeutic target for anticancer activity. Expert Rev Anticancer Ther, 2008. 8(9): p. 1461-70.

65. Azuma-Mukai, A., et al., Characterization of endogenous human Argonautes and their miRNA partners in RNA silencing. Proc Natl Acad Sci USA, 2008. 105(23): p. 7964-9.

66. Jackson, S. A., S. Koduvayur, and S. A. Woodson, Self-splicing of a group I intron reveals partitioning of native and misfolded RNA populations in yeast. RNA, 2006. 12(12): p. 2149-59.

67. Funston, G. M., et al., Expression of heterologous genes in oncolytic adenoviruses using picornaviral 2A sequences that trigger ribosome skipping. J Gen Virol, 2008. 89(Pt 2): p. 389-96.

68. Tong, A. W., et al., Intratumoral injection of INGN 241, a nonreplicating adenovector expressing the melanoma-differentiation associated gene-7 (mda-7/IL24): biologic outcome in advanced cancer patients. Mol Ther, 2005. 11(1): p. 160-72.

69. Hu, X., et al., Characterization of a unique factor-independent variant derived from human factor-dependent TF-1 cells: a transformed event. Leuk Res, 1998. 22(9): p. 817-26.

70. Santoli, D., et al., Synergistic and antagonistic effects of recombinant human interleukin (IL) 3, IL-1 alpha, granulocyte and macrophage colony-stimulating factors (G-CSF and M-CSF) on the growth of GM-CSF-dependent leukemic cell lines. J Immunol, 1987. 139(10): p. 3348-54.

71. Romero, P., Current state of vaccine therapies in non-small-cell lung cancer. Clin Lung Cancer, 2008. 9 Suppl 1: p. S28-36.

72. Robinson, J., et al., The European searchable tumour line database. Cancer Immunol Immunother, 2009.

What is claimed is:

1. An expression vector comprising:
   a first nucleic acid insert operably linked to a promoter, wherein the first insert encodes a Granulocyte Macrophage Colony Stimulating Factor (GM-CSF) cDNA sequence; and
   a second nucleic acid insert operably linked to the promoter, wherein the second insert encodes a bi-functional short hairpin RNA (bi-shRNA), wherein the bi-shRNA comprises:
   (a) a first stem loop structure comprising
      (i) a first guide sequence capable of hybridizing to a region of a mRNA transcript corresponding to base sequences 300-318, 731-740, 1967-1991, 2425-2444, 2827-2851, or 2834-2852 of SEQ ID NO:2; and
      (ii) a first passenger sequence fully complementary to the first guide sequence; and
   (b) a second stem loop structure comprising
      (i) a second guide sequence capable of hybridizing to a region of an mRNA transcript corresponding to base sequences 300-318, 731-740, 1967-1991, 2425-2444, 2827-2851, or 2834-2852 of SEQ ID NO:2; and
      (ii) a second passenger sequence partially complementary to the second guide sequence.

2. The expression vector of claim 1, further comprising a nucleic acid sequence encoding a picornaviral 2A ribosomal skip peptide between the first and the second nucleic acid inserts.

3. The expression vector of claim 1, wherein the promoter is a cytomegalovirus (CMV) mammalian promoter.

4. The expression vector of claim 3, further comprising a CMV intermediate-early (IE) 5' UTR enhancer sequence and a CMV IE Intron A sequence.

5. The expression vector of claim 1, wherein the bi-shRNA targets a sequence within the 3' UTR region of a furin mRNA transcript.

6. A method of enhancing an immune response in an individual in need thereof, comprising administering to the individual a therapeutically effective amount of cells transfected with the expression vector of claim 1.

7. The method of claim 6, wherein the GM-CSF is human.

8. The method of claim 6, wherein the expression vector further comprises a nucleic acid encoding a picornaviral 2A ribosomal skip peptide between the first and the second nucleic acid inserts.

9. The method of claim 6, where the promoter is a CMV mammalian promoter, and wherein the expression vector further comprises a CMV enhancer sequence and a CMV intron sequence.

10. The method of claim 6, wherein the region targeted by the bi-shRNA is within the 3' UTR region sequence of a furin mRNA transcript.

11. The method of claim 6, wherein the region targeted by the bi-shRNA is within the coding region of a furin mRNA transcript.

12. The method of claim 6, wherein the cells are autologous tumor cells, xenograft expanded autologous tumor cells, or allogeneic tumor cells.

13. The method of claim 6, wherein the individual has a cancer.

14. The method of claim 6, wherein the therapeutically effective amount of cells is about $1 \times 10^7$ cells to about $2.5 \times 10^7$ cells.

15. The method of claim 6, wherein the composition further comprises a therapeutically effective dose of γIFN (gamma interferon).

16. The method of claim 15, wherein the therapeutically effective dose of γIFN is about 50 μg/m$^2$ or about 100 μg/m$^2$.

17. An expression vector comprising a nucleic acid insert encoding a bi-functional small hairpin RNA (bi-shRNA) operably linked to a promoter, wherein the bi-shRNA comprises:
   (a) a first stem loop structure comprising
      (i) a first guide sequence capable of hybridizing to a region of a mRNA transcript corresponding to base sequences 300-318, 731-740, 1967-1991, 2425-2444, 2827-2851, or 2834-2852 of SEQ ID NO:2; and
      (ii) a first passenger sequence fully complementary to the first guide sequence; and
   (b) a second stem loop structure comprising
      (i) a second guide sequence capable of hybridizing to a region of an mRNA transcript corresponding to base sequences 300-318, 731-740, 1967-1991, 2425-2444, 2827-2851, or 2834-2852 of SEQ ID NO:2; and
      (ii) a second passenger sequence partially complementary to the second guide sequence.

18. The expression vector claim 1, wherein the bi-shRNA targets a sequence within the coding region of a furin mRNA transcript.

* * * * *

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Sythetic peptide
<220> FEATURE:
<221> NAME/KEY: misc_feature
<222> LOCATION: (2)..(2)
<223> OTHER INFORMATION: Xaa can be any naturally occurring amino acid
```

<400> SEQUENCE: 1

Arg Xaa Lys Arg Arg
1               5

<210> SEQ ID NO 2
<211> LENGTH: 4180
<212> TYPE: DNA
<213> ORGANISM: Homo sapiens

<400> SEQUENCE: 2

```
gcggggaagc agcagcggcc aggatgaatc ccaggtgctc tggagctgga tggtgaaggt    60
cggcactctt caccctcccg agccctgccc gtctcggccc catgccccca ccagtcagcc   120
ccgggccaca ggcagtgagc aggcacctgg gagccgaggc cctgtgacca ggccaaggag   180
acgggcgctc cagggtccca gccacctgtc cccccatggg agctgaggcc ctggttgcta   240
tgggtggtag cagcaacagg aaccttggtc ctgctagcag ctgatgctca gggccagaag   300
gtcttcacca acacgtgggc tgtgcgcatc cctggaggcc cagcggtggc caacagtgtg   360
gcacggaagc atgggttcct caacctgggc cagatcttcg gggactatta ccacttctgg   420
catcgaggag tgacgaagcg gtccctgtcg cctcaccgcc cgcggcacag ccggctgcag   480
agggagcctc aagtacagtg gctggaacag caggtggcaa agcgacggac taaacgggac   540
gtgtaccagg agcccacaga ccccaagttt cctcagcagt ggtacctgtc tggtgtcact   600
cagcgggacc tgaatgtgaa ggcggcctgg gcgcagggct acacagggca cggcattgtg   660
gtctccattc tggacgatgg catcgagaag aaccacccgg acttggcagg caattatgat   720
cctggggcca gttttgatgt caatgaccag gaccctgacc ccagcctcg gtacacacag   780
atgaatgaca caggcacgg cacacggtgt gcggggaag tggctgcggt ggccaacaac   840
ggtgtctgtg gtgtaggtgt ggcctacaac gcccgcattg aggggtgcg catgctggat   900
ggcgaggtga cagatgcagt ggaggcacgc tcgctgggcc tgaacccaa ccacatccac   960
atctacagtg ccagctgggg ccccgaggat gacggcaaga cagtggatgg ccagcccgc  1020
ctcgccgagg aggccttctt ccgtggggtt agccaggggcc gagggggct gggctccatc  1080
tttgtctggg cctcggggaa cggggggccgg gaacatgaca gctgcaactg cgacggctac  1140
accaacagta tctacacgct gtccatcagc agcgccacgc agtttggcaa cgtgccgtgg  1200
tacagcgagg cctgctcgtc cacactggcc acgacctaca gcagtggcaa ccagaatgag  1260
aagcagatcg tgacgactga cttgcggcag aagtgcacgg agtctcacac gggcacctca  1320
gcctctgccc ccttagcagc cggcatcatt gctctcaccc tggaggccaa taagaacctc  1380
acatggcggg acatgcaaca cctggtggta cagacctcga agccagccca cctcaatgcc  1440
aacgactggg ccaccaatgg tgtgggccgg aaagtgagcc actcatatgg ctacgggctt  1500
ttggacgcag cgccatggt ggccctggcc cagaattgga ccacagtggc cccccagcgg  1560
aagtgcatca tcgacatcct caccgagccc aaagacatcg ggaaacggct cgaggtgcgg  1620
aagaccgtga ccgcgtgcct gggcgagccc aaccacatca ctcggctgga gcacgctcag  1680
gcgcggctca ccctgtccta taatcgccgt ggcgacctgg ccatccacct ggtcagcccc  1740
atgggcaccc gctccaccct gctggcagcc aggccacatg actactccgc agatgggttt  1800
aatgactggg ccttcatgac aactcattcc tgggatgagg atcctctgg cgagtgggtc  1860
ctagagattg aaaacaccag cgaagccaac aactatggga cgctgaccaa gttcaccctc  1920
gtactctatg gcaccgcccc tgagggctg ccgtacctc cagaaagcag tggctgcaag  1980
```

```
accctcacgt ccagtcaggc ctgtgtggtg tgcgaggaag gcttctccct gcaccagaag    2040
agctgtgtcc agcactgccc tccagggttc gccccccaag tcctcgatac gcactatagc    2100
accgagaatg acgtggagac catccgggcc agcgtctgcg ccccctgcca cgcctcatgt    2160
gccacatgcc aggggccggc cctgacagac tgcctcagct gccccagcca cgcctccttg    2220
gaccctgtgg agcagacttg ctcccggcaa agccagagca gccgagagtc cccgccacag    2280
cagcagccac ctcggctgcc cccggaggtg gaggcgggc aacggctgcg ggcagggctg     2340
ctgccctcac acctgcctga ggtggtggcc ggcctcagct gcgccttcat cgtgctggtc    2400
ttcgtcactg tcttcctggt cctgcagctg cgctctggct ttagttttcg gggggtgaag    2460
gtgtacacca tggaccgtgg cctcatctcc tacaaggggc tgcccctga  agcctggcag    2520 gaggagtgcc cgtctgactc agaagaggac gagggccggg gcgagaggac cgcctttatc    2580
aaagaccaga gcgccctctg atgagcccac tgcccacccc ctcaagccaa tccctccttt    2640
gggcactttt taattcacca aagtattttt ttatcttggg actgggtttg accccagct    2700 ggggaggcaag aggggtggag actgcttccc atcctaccct cgggcccacc tggccacctg   2760
aggtgggccc aggaccagct ggggcgtggg gagggccgta ccccacccctc agcacccctt   2820 ccatgtggag aaaggagtga aacctttagg gcagcttgcc ccggcccgg ccccagccag    2880 agttcctgcg gagtgaagag gggcagccct tgcttgttgg gattcctgac ccaggccgca    2940
gctcttgccc ttccctgtcc ctctaaagca ataatggtcc catccaggca gtcgggggct    3000
ggcctaggag atatctgagg gaggaggcca cctctccaag ggcttctgca ccctccaccc    3060
tgtcccccag ctctggtgag tcttggcggc agcagccatc ataggaaggg accaaggcaa    3120
ggcaggtgcc tccaggtgtg cacgtggcat gtggcctgtg gcctgtgtcc catgacccac    3180
ccctgtgctc cgtgcctcca ccaccactgg ccaccaggct ggcgcagcca aggccgaagc    3240
tctggctgaa ccctgtgctg gtgtcctgac caccctcccc tctcttgcac ccgcctctcc    3300
cgtcagggcc caagtccctg ttttctgagc ccgggctgcc tgggctgttg gcactcacag    3360
acctggagcc cctgggtggg tggtggggag gggcgctggc ccagccggcc tctctggcct    3420
cccacccgat gctgctttcc cctgtgggga tctcaggggc tgtttgagga tatattttca    3480
ctttgtgatt atttcacttt agatgctgat gatttgtttt tgtattttta atgggggtag    3540
cagctggact acccacgttc tcacacccac cgtccgccct gctcctccct ggctgccctg    3600
gccctgaggt gtggggggctg cagcatgttg ctgaggagtg aggaatagtt gagccccaag   3660
tcctgaagag gcgggccagc caggcgggct caaggaaagg gggtcccagt gggaggggca    3720
ggctgacatc tgtgtttcaa gtggggctcg ccatgccggg ggttcatagg tcactggctc    3780
tccaagtgcc agaggtgggc aggtggtggc actgagcccc cccaacactg tgccctggtg    3840
gagaaagcac tgacctgtca tgcccccctc aaacctcctc ttctgacgtg cctttttgcac   3900 ccctcccatt aggacaatca gtccctcccc atctgggagt ccccttttct tttctaccct    3960
agccattcct ggtacccagc catctgccca ggggtgcccc ctcctctccc atcccccctgc   4020 cctcgtggcc agcccggctg ttttgtaag atgctgggtt ggtgcacagt gattttttc     4080 ttgtaattta aacaggccca gcattgctgg ttctatttaa tggacatgag ataatgttag    4140
aggttttaaa gtgattaaac gtgcagacta tgcaaaccag                          4180
```